US010718763B2

United States Patent
Konry et al.

(10) Patent No.: US 10,718,763 B2
(45) Date of Patent: Jul. 21, 2020

(54) MICRODROPLET BASED BIOASSAY PLATFORM

(71) Applicant: Northeastern University, Boston, MA (US)

(72) Inventors: Tania Konry, Boston, MA (US); Pooja Sabhachandani, Boston, MA (US); Saheli Sarkar, Boston, MA (US)

(73) Assignee: Northeastern University, Boston, MA (US)

( * ) Notice: Subject to any disclaimer, the term of this patent is extended or adjusted under 35 U.S.C. 154(b) by 42 days.

(21) Appl. No.: 15/744,198

(22) PCT Filed: Jul. 15, 2016

(86) PCT No.: PCT/US2016/042677
§ 371 (c)(1),
(2) Date: Jan. 12, 2018

(87) PCT Pub. No.: WO2017/011819
PCT Pub. Date: Jan. 19, 2017

(65) Prior Publication Data
US 2018/0203005 A1    Jul. 19, 2018

Related U.S. Application Data

(60) Provisional application No. 62/192,958, filed on Jul. 15, 2015, provisional application No. 62/291,933, filed on Feb. 5, 2016.

(51) Int. Cl.
*G01N 33/543* (2006.01)
*G01N 33/569* (2006.01)
(Continued)

(52) U.S. Cl.
CPC ..... *G01N 33/5432* (2013.01); *B01F 13/0071* (2013.01); *B01L 3/0241* (2013.01);
(Continued)

(58) Field of Classification Search
None
See application file for complete search history.

(56) References Cited

U.S. PATENT DOCUMENTS

2009/0068170 A1* 3/2009 Weitz .................. G01N 33/505
424/130.1
2013/0052648 A1 2/2013 Yarmush et al.
(Continued)

FOREIGN PATENT DOCUMENTS

WO 2014107698 A1 7/2014
WO WO-2015031190 A1 * 3/2015 ............... C12Q 1/02

OTHER PUBLICATIONS

Baret, J. C., et al. "Fluorescence-activated droplet sorting (FADS): efficient microfluidic cell sorting based on enzymatic activity", Lab on a Chip, vol. 9 | No. 13 | 7 Jul. 7, 2009 | pp. 1850-1858: ISSN: 1473-0197 , DOI: 10.1039/b902504a.
(Continued)

*Primary Examiner* — Changhwa J Cheu
(74) *Attorney, Agent, or Firm* — Verrill Dana, LLP

(57) ABSTRACT

Platform technology involving aqueous microdroplet reaction vessels created, arrayed, and characterized by imaging microscopy in a microfluidic device are applied to a wide variety of bioassays involving the detection and phenotypic characterization of single cells. The bioassays include the rapid and automated detection of microbial pathogens and their antibiotic sensitivity from patient samples as well as the characterization of immune responses using a patient's own cells, including the killing of tumor cells.

8 Claims, 25 Drawing Sheets

(51) Int. Cl.
    *G01N 33/574*     (2006.01)
    *G01N 33/68*     (2006.01)
    *G01N 35/08*     (2006.01)
    *B01F 13/00*     (2006.01)
    *B01L 3/02*     (2006.01)
    *B01L 3/00*     (2006.01)
    *G01N 33/533*     (2006.01)

(52) U.S. Cl.
    CPC ... *B01L 3/502761* (2013.01); *B01L 3/502784* (2013.01); *G01N 33/54346* (2013.01); *G01N 33/56911* (2013.01); *G01N 33/56966* (2013.01); *G01N 33/57492* (2013.01); *G01N 33/6863* (2013.01); *G01N 35/08* (2013.01); *B01L 2200/0668* (2013.01); *G01N 33/533* (2013.01)

(56) References Cited

U.S. PATENT DOCUMENTS

2013/0190196 A1     7/2013     Onderdonk et al.
2014/0158233 A1     6/2014     Leslie et al.

OTHER PUBLICATIONS

Konry, T., et al., "Live single cell functional phenotyping in droplet nano-liter reactors", Scientific Reports, vol. 3, No. 1, 3179; DOI: 10.1038/srep03179 (2013).

Cho, S., et al., "Droplet-Based Microfluidic Platform for High-Throughput, Multi-Parameter Screening of Photosensitizer Activity", Analytical Chemisty, 2013, 85, (18) pp. 8866-8872, DOI: 10.1021/ac4022067 American Chemical Society.

Du, G., et al., "Cell-Based Drug Combination Screening with a Microfluidic Droplet Array System", American Chemical Society, 2013, 85 (14), pp. 6740-6747, DOI: 10.1021/ac400688f.

Sabhachandani, P., et al., "ScanDrop Diagnostic Approach for Detection of Bacterial Infection Markers", RISE: 2015, Reseach, Innovation and Scholarship Expo, Northeastern University, Abstract ID# 823.

Golbberg, A., et al., "Cloud-Enabled Microscopy and Droplet Microfluidic Platform for Specific Detection of *Escherichia coli* in Water", Jan. 2014, PLoS ONE, 9(1) pp. 1-9: e86341. doi:10.1371/journal.pone.0086341.

Cohen, N. et al., "Approaching near real-time biosensing: microfluidic microsphere based biosensor for real-time analyte detection.", Biosensors and Bioelectronics, vol. 66, Apr. 15, 2015, pp. 454-460. doi: 10.1016/j.bios.2014,11.018.

\* cited by examiner

FIG. 10B
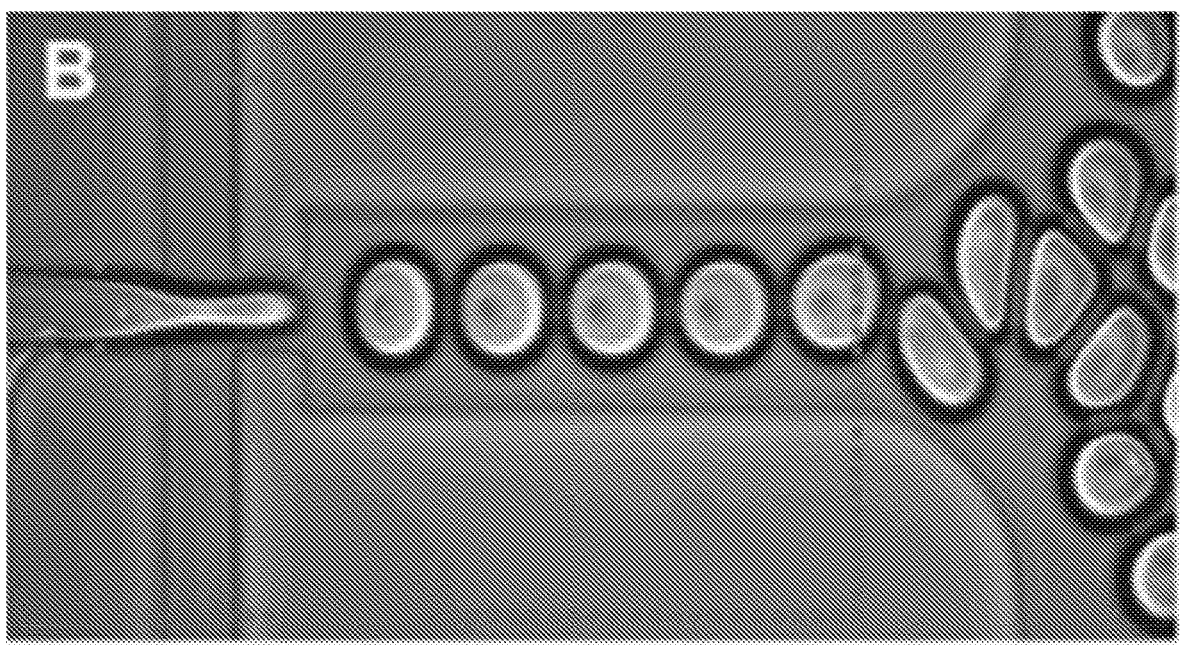
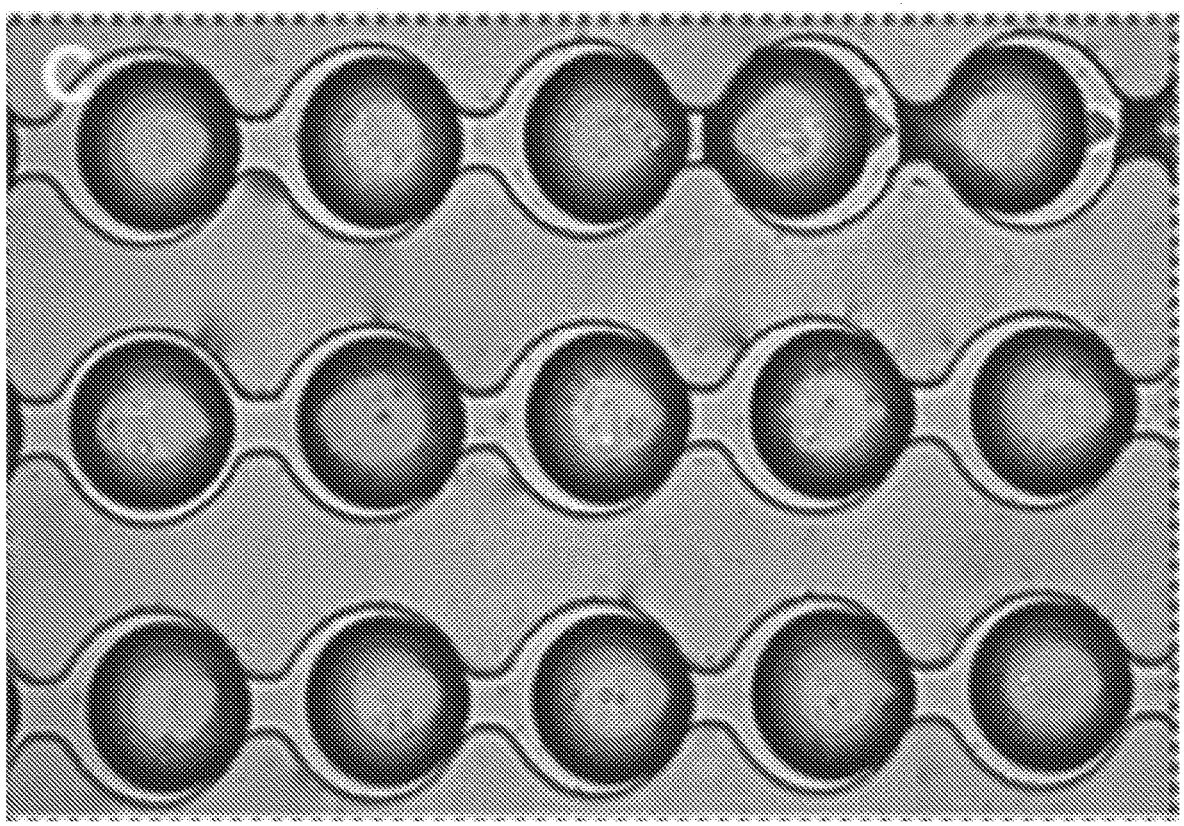
FIG. 10C

FIG. 10D
FIG. 10F
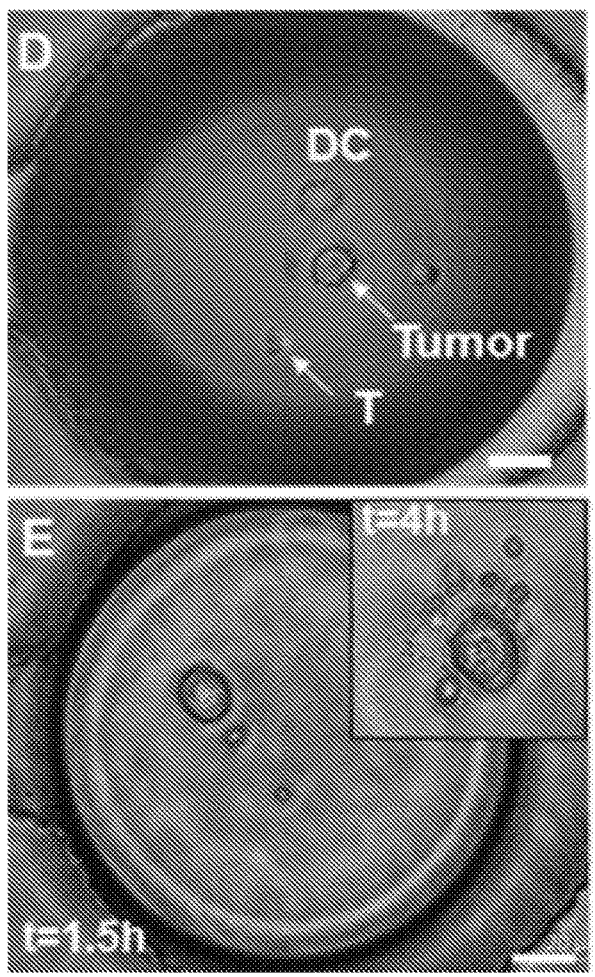
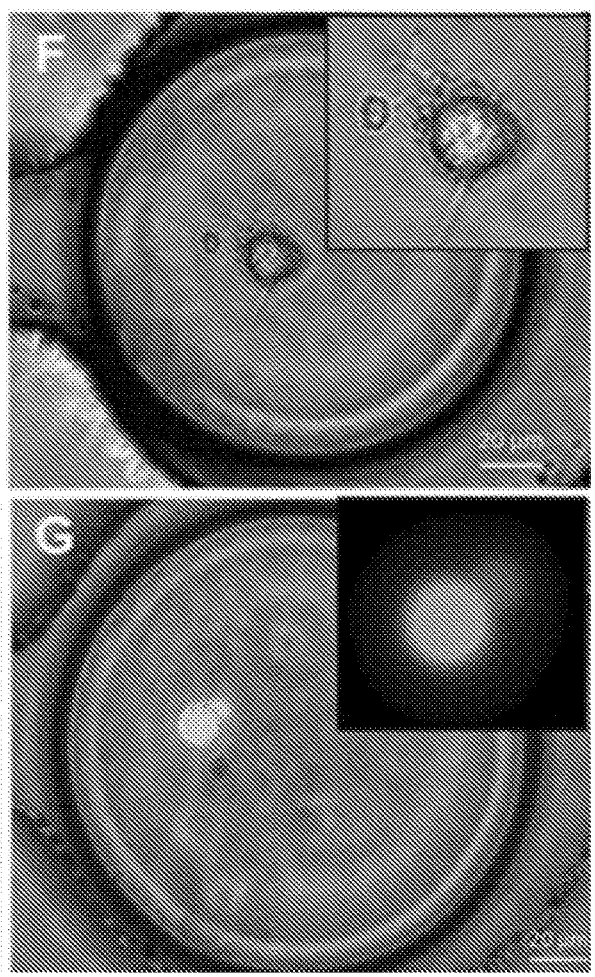
FIG. 10E
FIG. 10G

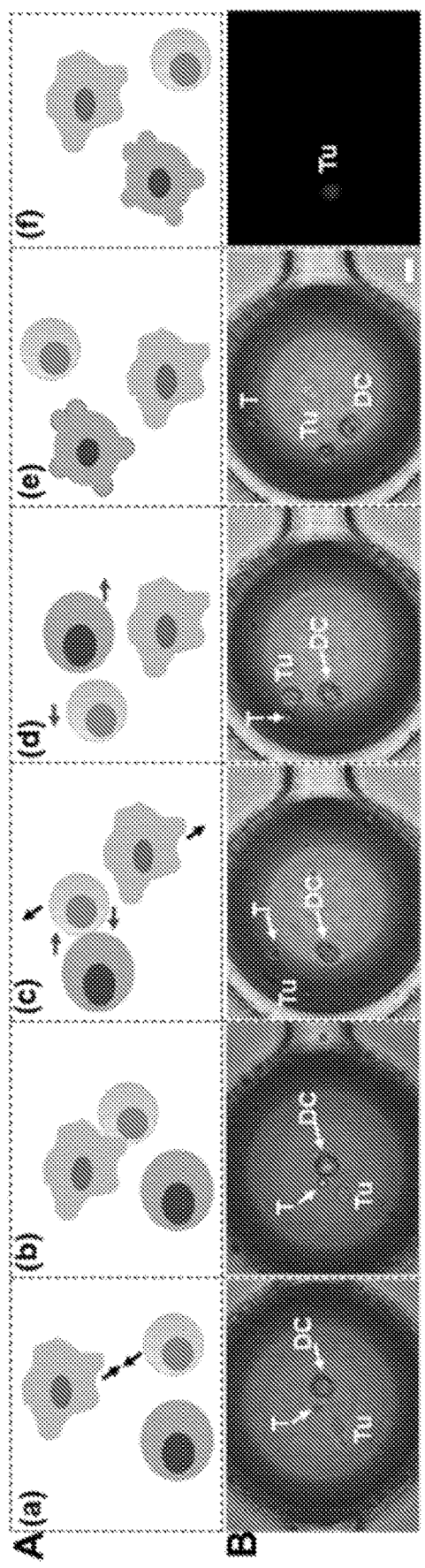
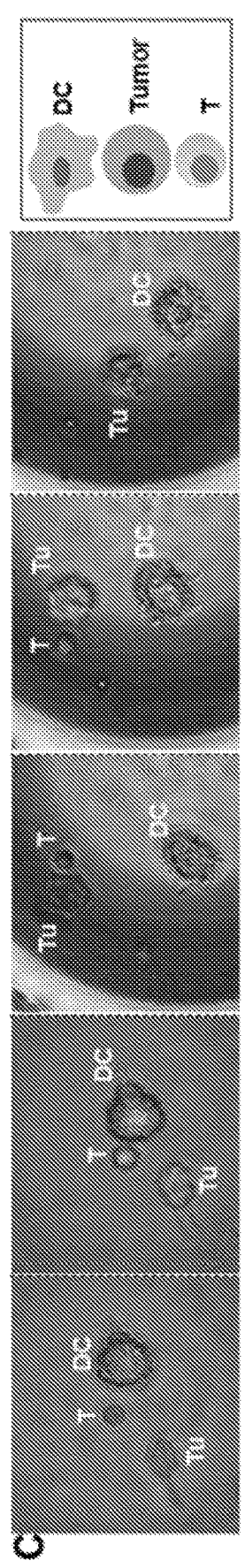
FIG. 12A
FIG. 12B
FIG. 12C

MICRODROPLET BASED BIOASSAY PLATFORM

CROSS REFERENCE TO RELATED APPLICATIONS

This application claims the priority of U.S. Provisional Application No. 62/192,958 filed 15 Jul. 2015 and entitled "Functional Phenotyping of Cells in Droplet Based Platforms" and of U.S. Provisional Application No. 62/291,933, filed 5 Feb. 2016 and entitled "Platforms for Microbial Detection and Phenotypic Drug Analysis". The whole of these provisional applications is hereby incorporated by reference.

STATEMENT REGARDING FEDERALLY SPONSORED RESEARCH OR DEVELOPMENT

This invention was made with government support under Grant Number CA174401 awarded by the National Institutes of Health. The government has certain rights in the invention.

BACKGROUND

The rapid emergence of antibiotic resistance, and decline in discovery of new antibiotics, has created a significant gap in the effective management of microbial infections. Additionally, persistent use of antibiotics in agriculture has further increased antibiotic resistant bacteria strains, thus making antibiotic resistant microbial infections an acute public health concern. According to the WHO global surveillance report for antimicrobial resistance, very high rates of resistance have been observed in common bacterial strains such as *Escherichia coli, Klebsiella pneumonia* and *Staphylococcus aureus* (apps.who.int/iris/bitstream/10665/112642/1/9789241564748_eng.pdf?ua=).

*E. coli* related urinary tract infections (UTIs) are among the most frequently encountered bacterial infections in the United States (1,2) with an annual incidence of over 8 million. Infection may involve both lower (bladder, cystitis) and upper urinary tract (kidney, pyelonephritis) and lead to significant morbidity, including permanent kidney damage (chronic pyelonephritis) or life threatening bacterial sepsis. The cumulative morbidity is profound with over 100,000 hospitalizations per annum. (3)

Appropriate treatment of UTI is critical for optimal outcome and requires use of agents that are active against the infecting pathogen. In the outpatient setting, patients are often prescribed empiric antibiotic therapy as susceptibility patterns of uropathogens have, until recently, been generally predictable. In hospitalized patients, empiric therapy is given for 48-72 hours until traditional culture results and susceptibility data are available. However, the rapid emergence of antibiotic resistance in recent years presents a significant challenge for UTI management.(4-8) In particular, carbapenem-resistant and extended-spectrum β-lactamase producing Enterobacteriaceae are an immediate public health threats, as they express resistance to commonly used empiric antimicrobial regimens. (9-11) Pathogens amongst the ESKAPE group are predicted to become resistant to currently available antibiotics within the next decade. Alarmingly, these are amongst the most common agents of UTI seen in hospitalized patients.

Initiation of active, appropriate antimicrobial patient therapy is ultimately dependent upon turnaround time of infection diagnostic methods. (12) Historically, this testing has relied on routine culture to isolate organisms; biochemical tests for bacterial identification; and culture based antibiotic susceptibility testing (AST). (13) However, using traditional technology, susceptibility results are generally not available for 48-72 hours. This means that for the first three days of suspected infection, therapy is largely unguided. Therefore, the ability to shrink this window by rapidly performing AST for bacterial pathogens is urgently needed. Rapid AST will also decrease emergence of resistance by allowing targeted (antibiotic de-escalation) or discontinuation of therapy if bacterial infection is ruled out (14,15).

New technologies have been applied to address this problem (16). For example, MALDI-TOF mass spectrometry (MS) and nucleic acid amplification tests (NAATs) are beginning to transform the clinical microbiology laboratory. These newer platforms offer several benefits over traditional culture methods; however, they also have significant limitations. MS is generally rapid and can identify a large database of bacteria. However, lengthy culture pre-amplification is still required, since analysis can only be performed on isolated bacterial colonies. (17) Also, MS-based AST only marginally decreases the time needed to identify organisms and does not address the need for rapid AST. Lastly, MS equipment is expensive ($200,000-300,000), bulky, complex to operate, and requires regular maintenance. (16) Therefore, MS systems must be placed in a centralized laboratory, away from the site of patient care, further delaying access to diagnostics.

Alternatively, NAATs have the capability to identify specific organisms or resistance genes directly from a clinical sample within two hours, including sample preparation. (18-21) However, they fall short in their ability to yield a comprehensive resistance profile. Specifically, resistance mechanisms are often multifactorial. Therefore, even highly multiplexed NAATs cannot accurately predict phenotypic susceptibility. (22) For example, resistance to a carbapenem in Gram negative bacilli (GNB) may reflect contributions from multiple β-lactamases, porins, and efflux pumps. Indeed, a GNB producing the New Delhi metallo-β-lactamase 1 (NDM-1) enzyme may carry up to eight plasmids (5) together encoding scores of resistance elements that may interact in unexpected ways. (23) Therefore, the Clinical and Laboratory Standards Institute (CLSI) now recommends using carbapenem MIC as the sole criterion for assessing susceptibility, as the mere presence or absence of a CRE genetic element alone does not predict phenotypic response.

Heterogeneity in single cell responses arises from intrinsic stochasticity in both transcription and translation, thereby leading to significant variability in quantitative levels of mRNA and protein within cell populations. This results in biological noise, which can be further enhanced by minor differences in environmental stimuli, variations in cell state and polyfunctional responses. This heterogeneity is an essential characteristic of cellular systems and must be assessed by analyzing individual cell behavior. Furthermore, the dynamic nature of biological processes occurs at varying time scales, requiring continuous real-time evaluation of single cell outcomes. This is particularly evident in analysis of immune responses, which involve a variety of cell types.

Currently, flow cytometry is the most useful technique for single cell analysis, due to its high-throughput and multiplexing capability. However, it cannot provide time-varying spatiotemporal resolution of signaling dynamics in the same cell. Other single cell analysis techniques include laser scanning cytometry, capillary electrophoresis and laser capture microdissection. Many of these techniques suffer from limitations of throughput and complicated operation.

Microfluidic single cell analysis tools have emerged as a powerful alternative to conventional cell culture techniques with respect to throughput, multiplexing, sensitivity, and robust control of cellular microenvironment. Single cells have been captured by valve-based methods (67), dielectrophoretic mechanisms (68,69), and optical tweezers (70). However, active mechanisms such as dielectric forces can negatively impact cell viability; additionally, the throughput achieved with these methods is generally low. Microwells utilize passive gravity-based methods to allow single cell sedimentation followed by stimulation of cells (71, 72). However, non-adherent cells could potentially be lost from their holding sites over time with this technology. Another commonly implemented method relies on manipulating fluid flow or employing hydrodynamic guiding features to direct cells towards traps, thus allowing cells to be sequestered in variously shaped docking structures (73-76). Hydrodynamic arrays have been extensively investigated to achieve optimal capture efficiency and single cell compartmentalization by assessing various trap structure, position and distance (77-80). However, a common limiting feature of most of these microfluidic approaches is the lack of isolation of a cell from its neighbors, leaving room for paracrine effects. Thus, there remains a need for new methods that allow cell function and cell-cell interactions to be analyzed in isolation.

SUMMARY OF THE INVENTION

The invention provides a fast, highly sensitive, direct-from-patient, microfluidic droplet-based bioassay platform that offers single cell based analysis for efficient monitoring of bacterial infection and cell function, as well as for high throughput testing of the susceptibility of single cells to antibiotics and other pharmaceutical agents. The methods and devices provided can be used to monitor bacteria and perform antibiotic susceptibility testing for urinary tract infection directly from patient samples with no or minimal pre-processing steps.

The bioassay platform is based on analysis of an array of single droplets using a microfluidics device coupled with a fluorescence microscopy imaging system. Cells are encapsulated in aqueous microdroplets suspended in an oil medium and directed, sorted, and arranged by the microfluidic device for analysis, which may include identification and quantification of the cells as well as characterization of cell phenotype, such as function, gene expression, presence or absence of biomarkers, or susceptibility to antiibiotics or other drugs. Various reagents for the analysis can be added to the droplets at formation or by later merger of droplets. Such reagents include antibody-conjugated microspheres, fluorescent detection antibodies, cell viability indicators, antibiotics or drugs, and other cells for cell-cell interaction studies. The analysis of single droplets provides high sensitivity and short reaction times. A further advantage is the use of an on chip docking array, where up to hundreds or thousands of microdroplets can be maintained stably for long-term culture, such as to assess time-variant growth dynamics of encapsulated bacteria at single cell resolution or to study T-cell mediated killing of tumor cells, for example. Tracking individual cells such as bacteria over time can provide critical information on cellular heterogeneity based on characteristics such as cell division, density, morphology and antibiotic resistance.

The invention provides diagnostic methods for detecting and quantifying bacterial pathogens, including the most prevalent and antibiotic-resistant pathogens, without the need for culture or pre-amplification, and provide automated phenotypic analysis, including antibiotic susceptibility, within a few hours, such as 3 hours, of sample acquisition. Bacterial cells present in urine samples are co-encapsulated with various antibiotics at 1-4 cells in picoliter-volume droplets for determination of susceptibility within 1 hour by standard fluorescence microscopy imaging. The original patient sample concentration can be as low as 50000 CFU/mL. Furthermore, urine also can be analyzed to assess the state of inflammation in the patient by enumeration of white blood cells and cytokines, which aids in distinguishing true infection from sample contamination. IL-6 and IL-8 are produced by infected urothelial cells based on recognition of pathogen associated molecular patterns (24-27), and therefore provide a measure of inflammatory state, even in highly immunocompromised patients who do not mount a significant WBC response. (28,29)

Furthermore, the present microfluidics-based technology can be deployed with inexpensive portable instrumentation and disposables. The portability and low cost of consumables should permit distribution to sites of patient care in hospitals, primary care, and resource-limited settings, thereby accelerating personalized therapy and improving patient outcomes. The same qualities also make the technology ideal to identify infected patients efficiently for clinical trial enrollment.

The invention can be summarized further by the following list of embodiments:

1. A method of detecting bacterial cells, the method comprising the steps of:
   (a) providing a microfluidic device capable of forming aqueous microdroplets in oil, the device comprising a translucent microdroplet array chamber, and providing a fluorescence imaging microscope;
   (b) preparing a plurality of aqueous microdroplets in oil using the microfluidic device, each microdroplet comprising a sample containing or suspected of containing one or more bacterial cells, one or more microbeads conjugated with a capture antibody capable of specifically binding a selected type of bacterial cell at a first epitope, and a fluorescently labeled detection antibody capable of specifically binding the selected type of bacterial cell at a second epitope;
   (c) directing the plurality of aqueous microdroplets into the microdroplet array chamber;
   (d) obtaining a fluorescence image of the microdroplet array chamber using the fluorescence imaging microscope; and
   (e) measuring fluorescence emission from the labeled detection antibody in images of the microbeads, whereby the presence of the selected type of bacterial cell in the sample is detected when fluorescence emission from the labeled detection antibody overlaps with an image of one or more of said microbeads.

2. The method of embodiment 1, wherein in step (e) an intensity of said fluorescence emission is proportional to the number of bacteria bound to the microbead.

3. The method of embodiment 1 or embodiment 2 which is carried out in multiplex format using two or more types of microbeads, each type of microbeads conjugated with a capture antibody that specifically binds a different type of bacterial cell, and using two or more types of distinctly fluorescent labeled detection antibodies, and wherein two or more types of bacteria are detected simultaneously.

4. The method of embodiment 3, wherein each type of microbeads is labeled with a distinct fluorescent label, such as a unique concentration of a Europium dye associated with each type of microbeads.
5. The method of any of the previous embodiments, wherein one or more reagents are added to the aqueous microdroplets after their formation using a droplet merging junction.
6. The method of any of the previous embodiments, wherein aqueous microdroplets are sorted and routed to a selected fluidic pathway or chamber according to fluorescence detected in the aqueous microdroplets.
7. The method of any of the previous embodiments, wherein one or more aqueous microdroplets are routed outside the device for collection, further characterization, and/or culturing of bacterial cells contained therein.
8. The method of embodiment 7, wherein further characterization is performed comprising analyzing one or more genes or the expression thereof of a collected bacterial cell.
9. The method of any of the previous embodiments, further comprising analyzing a phenotype of one or more bacterial cells in an aqueous microdroplet.
10. The method of embodiment 9, wherein the phenotype is antibiotic sensitivity, and wherein the aqueous microdroplets comprise an antibiotic suspected of killing or hindering growth of the selected type of bacteria, and bacterial growth and/or viability in the microdroplet is assessed.
11. The method of any of the previous embodiments, wherein the sample is a patient sample selected from the group consisting of urine, blood, serum, plasma, sputum, or a lavage fluid.
12. The method of embodiment 11, wherein the patient sample is urine, and a urinary tract infection is diagnosed.
13. The method of embodiment 11, wherein the patient sample is blood, serum, or plasma, and sepsis is diagnosed.
14. The method of embodiment 11, wherein the patient sample is sputum or a lavage fluid, and a pulmonary or gastric infection is diagnosed.
15. The method of any of the previous embodiments, wherein the aqueous microdroplets further comprise one or more additional types of microbeads, each type conjugated with a capture antibody capable of specifically binding an analyte present in or suspected of being present in the sample, and one or more distinctly fluorescently labeled detection antibodies capable of specifically binding the analyte.
16. The method of embodiment 15, wherein the analyte is IL-6 or IL-8.
17. The method of any of the previous embodiments, wherein said microbeads are non-magnetic.
18. A method of analyzing a cell phenotype, the method comprising the steps of:
(a) providing a microfluidic device capable of forming aqueous microdroplets in oil, the device comprising a translucent microdroplet array chamber, and providing an imaging microscope;
(b) preparing a plurality of aqueous microdroplets in oil using the microfluidic device, each microdroplet comprising a sample containing or suspected of containing one or more cells and one or more reagents for analyzing a phenotype of said cells;
(c) directing the plurality of aqueous microdroplets into the microdroplet array chamber;
(d) obtaining an image of the microdroplet array chamber using the imaging microscope; and
(e) measuring an optical signal from said reagent, whereby information regarding the phenotype of said cells is obtained.
19. The method of embodiment 18, wherein the reagent is an antibody or antibody-conjugated microbead, a fluorescent dye, cell, nucleic acid, peptide, protein, vaccine, or pharmaceutical agent.
20. The method of embodiment 18 or embodiment 19, wherein the phenotype is cytokine secretion by the cells, and the reagents comprise a microbead conjugated capture antibody and a fluorescent labeled detection antibody, wherein both antibodies specifically bind to said cytokine.
21. The method of embodiment 18 or embodiment 19, wherein the phenotype is cell viability, and the reagents comprise a fluorescent indicator of live vs. dead cells.
22. The method of embodiment 18 or embodiment 19, wherein the phenotype is susceptibility to an antitumor agent, the cells comprise tumor cells, and the reagents comprise the antitumor agent.
23. The method of embodiment 18 or embodiment 19, wherein the phenotype is activation of an immune response, the cells comprise T lymphocytes, and the reagents comprise antigen presenting cells.
24. The method of embodiment 18 or embodiment 19, wherein the phenotype is the presence of a biomarker, and the reagents comprise a microbead conjugated capture antibody and a fluorescent labeled detection antibody, wherein the capture antibody specifically binds to an epitope on a selected cell type and the detection antibody specifically binds to said biomarker.
25. The method of embodiment 18 or embodiment 19, wherein the phenotype is the action of a pharmaceutical agent on the cells, and the reagents comprise an optical indicator of an effect of the pharmaceutical agent on the cells.
26. The method of any of embodiments 18-25 which is carried out in multiplex format, and two or more phenotypes are analyzed simultaneously.
27. The method of any of embodiments 18-26, wherein one or more additional reagents are added to the aqueous microdroplets after their formation using a droplet merging junction.
28. The method of any of embodiments 18-27, wherein aqueous microdroplets are sorted and routed to a selected fluidic pathway or chamber according to an optical signal detected in the aqueous microdroplets.
29. The method of any of embodiments 18-28, wherein one or more aqueous microdroplets are routed outside the device for collection, further characterization, and/or culturing of cells contained therein.
30. The method of any of embodiments 18-29, wherein phenotype analysis comprises analyzing one or more genes or the expression thereof of one or more of said cells.

BRIEF DESCRIPTION OF THE DRAWINGS

FIG. 1A shows a microdroplet array (left side) and a droplet distribution mechanism (right side).
FIG. 1B show a droplet merging junction.
FIG. 1C shows a sample droplet containing fluorescent microbeads detecting bound bacteria;
FIG. 1D is a schematic illustration of the components used in the microdroplet based detection of bacteria.

FIG. 4A presents a schematic illustration of the design. FIG. 4B shows droplet generation and droplet array of the device. FIG. 4C shows PDMS/glass chip optics for signal detection, and PR-PR to facilitate microscopy control and data acquisition.

FIGS. 10A-10G illustrate cell co-encapsulation in a droplet microfluidic platform. FIG. 10A shows a schematic of an integrated three-inlet droplet generation and microarray device. FIG. 10B shows the generation of nanoliter droplets. FIG. 10C shows droplets loaded in a microarray for stable docking. FIG. 10D shows co-encapsulation of three types of cells into droplets. FIG. 10E shows cellular exocytosis observed in a droplet. Inset shows a magnified image of vesicles secreted by DCs at 4 hours. FIG. 10F shows the morphology of single DC and T cells in a droplet. Inset shows a magnified image of a dendrite extension by a DC. FIG. 10G shows blebbing of cell membrane prior to cell death. Inset shows a fluorescence image of a cell (labeled with calcein-AM) membrane deformation. Scale bar: 20 µm.

FIG. 11A shows DCs that were pulsed with ovalbumin-FITC (100 µg/mL, 16 hours) and CCL21 (25 ng/mL, 2 hours) and co-encapsulated with untreated T cells in droplets. OVA-FITC expression on DC surface is indicated by arrowheads. T cells are labeled with CMTPX tracker, which is transferred to the DCs over time. Images were obtained every 5 minutes. Scale bar: 20 µm. FIG. 11B shows analysis of the types of interaction between DC and T cells: no interaction over a period of 5 hours, continuous interaction due to conjugate formation, and discontinuous interaction defined by short periods of attachment and detachment. DCs were either activated by pre-treatment with OVA-FITC and CCL21 (Ag activated) or untreated (Non activated). FIG. 11C shows cells undergoing discontinuous interaction, further categorized into transient (<10 minutes of contact) and stable (>10 minutes) interaction. FIG. 11D shows the distribution of contact times between DC and T cells (outliers are indicated).

FIGS. 12A-12C show co-encapsulation of tumor-lysate pulsed DC, T cells, and tumor cells (RPMI-8226 multiple myeloma cell line). FIG. 12A (top panel) illustrates the various stages of interaction between the immune and tumor cells below in FIGS. 12B (middle panel) and 12C (lower panel). Movement of DC and T cells are indicated by the black arrow while movement of T cells and tumor cells are indicated by the lighter arrow. Frames (a)-(e) depict sequential events. (a) Freely motile DC and T cells move towards each other within droplets. (b) DC-T cell conjugates are formed. (c) DC-T cell conjugates dissociate and cells become motile again. T cells and tumor cells move towards each other and establish contact. (d) T cells dissociate from tumor cell. (e) Tumor cells depict morphological changes, blebbing and membrane rupture. (f) Tumor cell death indicated by uptake of ethidium homodimer. FIG. 12B shows microscopic images of specific stages of interaction described in (A) observed in droplets. FIG. 12C shows magnified images of the corresponding panels shown in FIG. 12B. Scale bar: 20 µm.

FIG. 13A shows co-encapsulation of naïve T cell and DC stimulated with OVA-FITC (100 µg/mL). DCs demonstrate morphological change in droplets over time. FIG. 13B shows the increase in calcium transient in T cell following contact with DC. FIG. 13C show non-contact mediated increase in T cell calcium level. Insets of FIGS. 13B and 13C show: fluorescence images of the corresponding T cells. Scale bar: 50 µm. FIG. 13D shows representative traces of normalized fluorescent intensity (N.F.I) of Fluo-4 in T cells under various states of conjugation with DC:(a) DC-T cells in contact throughout experimental duration; (b) Cell contact initiated at t=2 min, indicated by the square and dissociated at t=12 min, indicated by the triangle; (c,d) No contact observed between DC and T cells throughout experimental duration.

DETAILED DESCRIPTION OF THE INVENTION

Figure 1B:
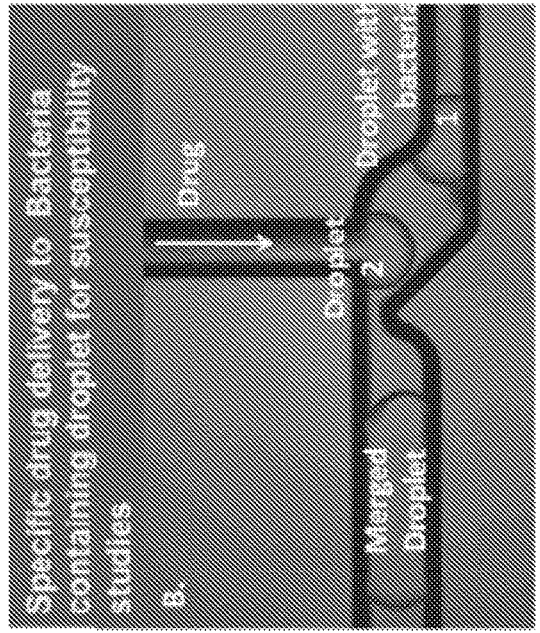
FIGS. 1A-1D show components of a microfluidic device for detection and quantification of bacterial cells in a fluid sample.
Figure 1A:
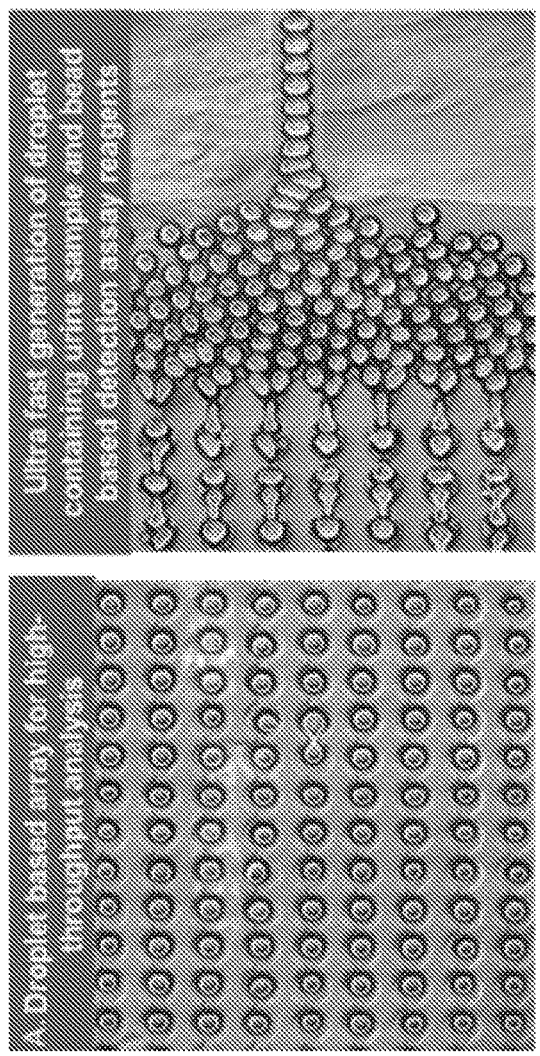
Figure 1D:
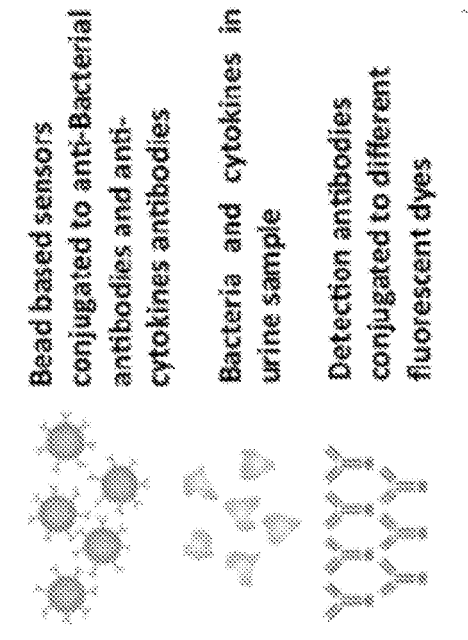
Figure 1D:
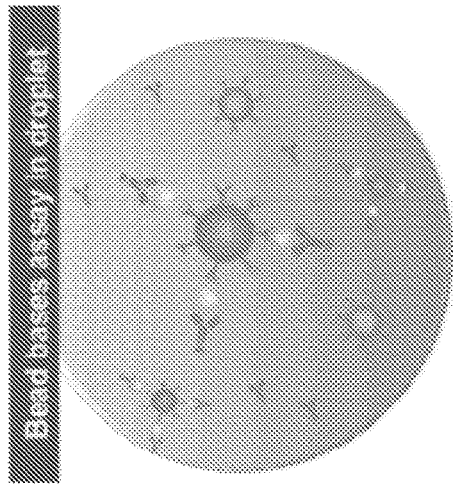
Figure 1C:
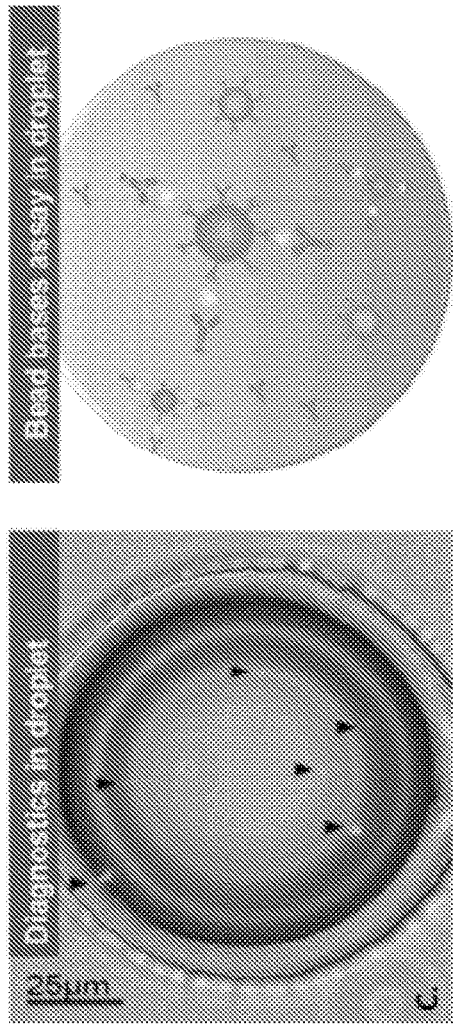

The microfluidic device of the invention allows for compartmentalizing a desired volume, up to and including the total volume, of a biological sample, or a dilution or concentrate thereof into micro-sized aqueous droplets, which serve as individual nanoliter reactors. The microdroplets can be used together with bead-based or other detection assay reagents to generate an incubation array of nanoliter droplets for analysis (FIG. 1A). The microfluidic device and its related methods of use for cell detection and analysis in microfluidic droplets constitute a platform or system for performing a wide variety of single cell-based bioassays. Furthermore, the platform also includes controlled delivery of reagents to cells for analysis; such reagents can include antimicrobials as well as cell proliferation and/or LIVE-DEAD assay reagents for susceptibility studies (FIG. 1B). The platform further allows simultaneous and automated monitoring of several reactions in the same microfluidic chip or reactor (i.e., multiplex diagnostic analysis), thus increasing throughput and decreasing time for detection and reagent use. The platform uses a two-phase system in which a sample containing live cells and bead-based and/or other assay reagents is compartmentalized into a series of individual aqueous microdroplets (1 pL to 10 nL volume per microdroplet) surrounded by an oil which is immiscible with water. (38-45) Advantages of this droplet-based technique include the physical and chemical isolation of droplets, eliminating the risk of cross-contamination; the fast and efficient mixing of reagents and gases that occurs inside droplets; the ability to digitally manipulate droplets at a very high throughput rate (up to 1000 droplets/sec); the ability to incubate stable droplets off-chip and reintroduce them into the microfluidic environment for further processing and analysis; and the absence of moving parts on the chip, such as integrated valves or pumps. (38-45) Further, the nanoliter microenvironment allows efficient gas exchange which is necessary to ensure viability of encapsulated cells for use in susceptibility testing.

In certain embodiments, antibody-conjugated microbeads are co-encapsulated with patient samples in microdroplets to provide an ultrasensitive, specific, and fast immunoassay. (46) For example, bacteria can be captured on a bead surface and then specifically identified through binding of a fluorescently labeled detection antibody. Thus, live bacterial cells present in a patient sample are captured and then detected on a bead surface allowing the detection resolution of one or more bacterial cells per bead in from about 5 minutes to about 2 hours, such as in about 10, 20, 30, 40, 50, 60, 90, 100, or 120 minutes. The high throughput droplet generation is typically at a rate of about 200 pL total droplet volume per second, and analysis capability by fluorescent imaging is about 500-1000 droplets per second, allowing screening the total sample volume directly (e.g., 100 µl sample of urine or BAL fluid) in <1 hour and determining phenotypic susceptibility results within 3 hours. The same microbead-based immunoassay technology can be used simultaneously to quantify cytokines of interest in the same microdroplets. (47) In addition, the system can operate as a fluorescence-activated droplet sorting (FADS) system, interrogating the entire reaction volume and sorting the resulting droplets based on the results. However, unlike other forms of droplet sorting, the bacterial cells remain encapsulated in droplets and can be identified individually post-sorting. This property allows efficient pathogen isolation after detection for susceptibility studies.

Herein, disclosed is a robust, multiplex platform for rapid microbial diagnostics, antimicrobial susceptibility testing, and use of inflammatory makers for prognostic profiling. In particular, an ultra-sensitive assay has been developed for detection of the most common causes of multidrug-resistant UTI: *Escherichia coli, Klebsiella pneumoniae, Enterobacter, Pseudomonas aeruginosa,* and *Proteus*. The generated bead-based sensor can be used to specifically and sensitively detect a bacterial level of 1000 to >100000 CFU/ml of urine, consistent with clinically relevant levels found in patients with UTI. Furthermore, the bead-based assay can be adapted for multiplex analysis of several pathogens simultaneously. The ability to perform such multiplex assay experiments facilitates the completion of patient sample analysis for possible causes of disease as well as reduce reagent cost and turnaround time. In particular, different beads have been generated that can be analyzed simultaneously by encoding each probe-functionalized bead type via an avidin-biotin bridge with a specific bacterial capturing antibody. Such beads previously have been functionalized with different antibody probes for simultaneous analyte detection. (47-51) In addition, the same bead-based approach is used for analysis of the inflammatory cytokine profile.

The devices and method of the present invention can be used to detect, quantify, and/or characterize a phenotype of bacteria or other cellular microbes present in a wide variety of infections or other pathological conditions. For example, they can be used in connection with microbes underlying urinary tract infections, such as *Escherichia coli, Enterococcus faecalis, Proteus mirabilis, Stenotrophomonas maltophilia, Staphylococcus saprophyticus, Pseudomonas aeruginosa, Enterobacteriaceae* species, *Klebsiella* species, and a fungus, *Candida albicans*. They can be used in connection with microbes underlying sepsis, including *Escherichia coli, Klebsiella pneumoniae, Pseudomonas aeruginosa, Streptococcus pneumoniae, Streptococcus pyogenes, Staphylococcus aureus, Enterobacter species, Proteus* species, and *Candida albicans*. They can be used in connection with microbes underlying pulmonary infections, such as *Pseudomonas aeruginosa, Klebsiela pneumoniae, Streptococcus pneumoniae, Haemophilus* species, *Staphylococcus aureus* and *Mycobacterium tuberculosis*. They can be used in connection with microbes underlying gastrointestinal infections, such as *Helicobacter pylori, Escherichia coli, Salmonella, Shigella, Campylobacter jejuni, Staphylococcus* and *Yersinia*.

Also disclosed is integration of the bead assay into a droplet-based microfluidics device that allows for co-encapsulation of the biological sample and bead-based bioassay reagents for bacterial and cytokine capture and later detection. Compared to standard bulk immunosorbent assays, the microfluidic droplet platform presented here reduces the reagent volume by four orders of magnitude per reaction, while fast reagent mixing reduces the detection time from hours to minutes. This platform is a significant leap forward in diagnostic assay miniaturization. Also contemplated is the use of droplet merging technology, which allows delivery of the antibiotics or other reagents into each droplet that contains previously-captured bacteria for susceptibility testing. Antibiotic growth inhibition and bactericidal activity is detected using optical and fluorescence based data integration.

Use of the system for detection and susceptibility testing of pathogens in patient urine samples is disclosed. Assay readout is optimized to yield qualitative (species) and quantitative (e.g., CFU/mL) readout, which is sufficient to establish UTI based on clinical cutoffs used for diagnosis. Furthermore, the ability of the system to determine susceptibility of isolates against select antimicrobials has been performed. In addition, the use of multiplex evaluation inclusive of cytokine measurements allows for predicting those patients at greatest risk of pyelonephritis, sepsis, and hospitalization. This patient group can then be targeted for early aggressive treatment with directed antimicrobial therapy to mitigate morbidity.

Characterization of the heterogeneity in immune reactions requires assessing dynamic single cell responses as well as interactions between the various subsets of immune cell subsets. However, there are currently few methods available that allow dynamic investigation of immune cell interactions, and other types of interactions among freely dispersed cells, without physically constraining the non-adherent cells. However, the microfluidic droplet microarray platform of the present invention permits rapid functional analysis of single cell responses and co-encapsulation of heterotypic cell pairs, thereby making possible the evaluation of the dynamic activation state of primary T cells, and other cellular functions and phenotypes.

The microfluidic device and methods of the present invention, through their ability to isolate and maintain single cells, pairs of cells, or small groups of three or more cells, make it possible to analyze various cell phenotypes and cell-cell interactions. These include, but are not limited to, cell viability, susceptibility of tumor cells to an antitumor agent, activation of an immune response (such as activation of T lymphocytes, B lymphocytes, dendritic cells, or other immune system cells), the effectiveness of a cellular vaccine (such as a dendritic cell vaccine), the presence or absence of a biomarker, and the action of a pharmaceutical agent on a target cell or non-target cell of interest (i.e., generation of dose-response curves or the determination of inhibition constants or binding or dissociation constants, or the observation of cellular level signal transduction events related to the mechanism of action of a drug or a side effect of a drug). Of particular importance is the ability to study the responsiveness of a patient's own immune cells against a tumor of the patient. This can be useful to evaluate the effectiveness of a cellular vaccine. The cancer can be, for example, a solid tumor, liquid tumor, hematologic tumor, renal cell cancer, melanoma, breast cancer, prostate cancer, testicular cancer, bladder cancer, ovarian cancer, cervical cancer, stomach cancer, esophageal cancer, pancreatic cancer, lung cancer, neuroblastoma, glioblastoma, retinoblastoma, leukemia, myeloma, lymphoma, hepatoma, adenoma, sarcoma, carcinoma, blastoma, or cancer of the colon, lung, kidney, liver, endometrium, cervix, ovary, thyroid, skin, or central nervous system. Several specific uses for cell phenotype assays are summarized in the examples below.

EXAMPLES

Example 1: Microsphere-Based Assay for Simultaneous Analytical Detection of Common Uropathogens Common causative agents for UTI, including *Escherichia coli*, *Klebsiella pneumoniae*, *Enterobacter*, *Pseudomonas aeruginosa*, and *Proteus*, can be detected in a multiplex assay. Multiplex bead array assays can be found as far back as 1977. (50-54) A wide assortment of tests have been devised for bead-based assays using both immunological and molecular ligands. However, a robust bead-based assay to capture and analyze bacteria has not yet been developed. Here, a bead-based protocol is disclosed with ultrahigh detection sensitivity and specificity of antigen-antibody reactions to identify bacterial presence in urine samples. The multiplex capabilities of the assay were used to detect several bacterial pathogens in urine samples simultaneously. The developed bead based detection protocol was validated for specificity and sensitivity as well as calibrated for determining the bacterial inoculum in the sample.

Preparation of a Bead Sensor for Bacteria and Cytokine Detection

So called "bar-coded" microbeads have been used in bead-based arrays (i.e., in suspension or liquid arrays). These techniques have several advantages over capturing bacteria on a flat surface such as an ELISA plate: (1) Beads can have larger surface areas than planar chips. This means that more captured bacteria can be immobilized on the bead, and, thus, bead-based arrays are more likely to detect a wide range of target pathogens. (2) Detection is faster and sensitivity is equal to or higher than that of ELISAs because the interaction between beads and target molecules can be nearly comparable with solution-phase kinetics. (3) Target molecules can be collected by using flow cytometry such as fluorescence-activated cell sorting (FACS), such as an automated plate-based BD FACSArray™ bioanalyzer, BD FACS™. (4) Large-scale fabrication and surface modification is possible, and the prepared beads can be stored. Thus, customization is possible by selective mixing of antibody-conjugated microbeads. (5) Beads can be used with a combination of microfluidic devices to detect trace amounts of bacteria in an automated manner.

Figure 2:
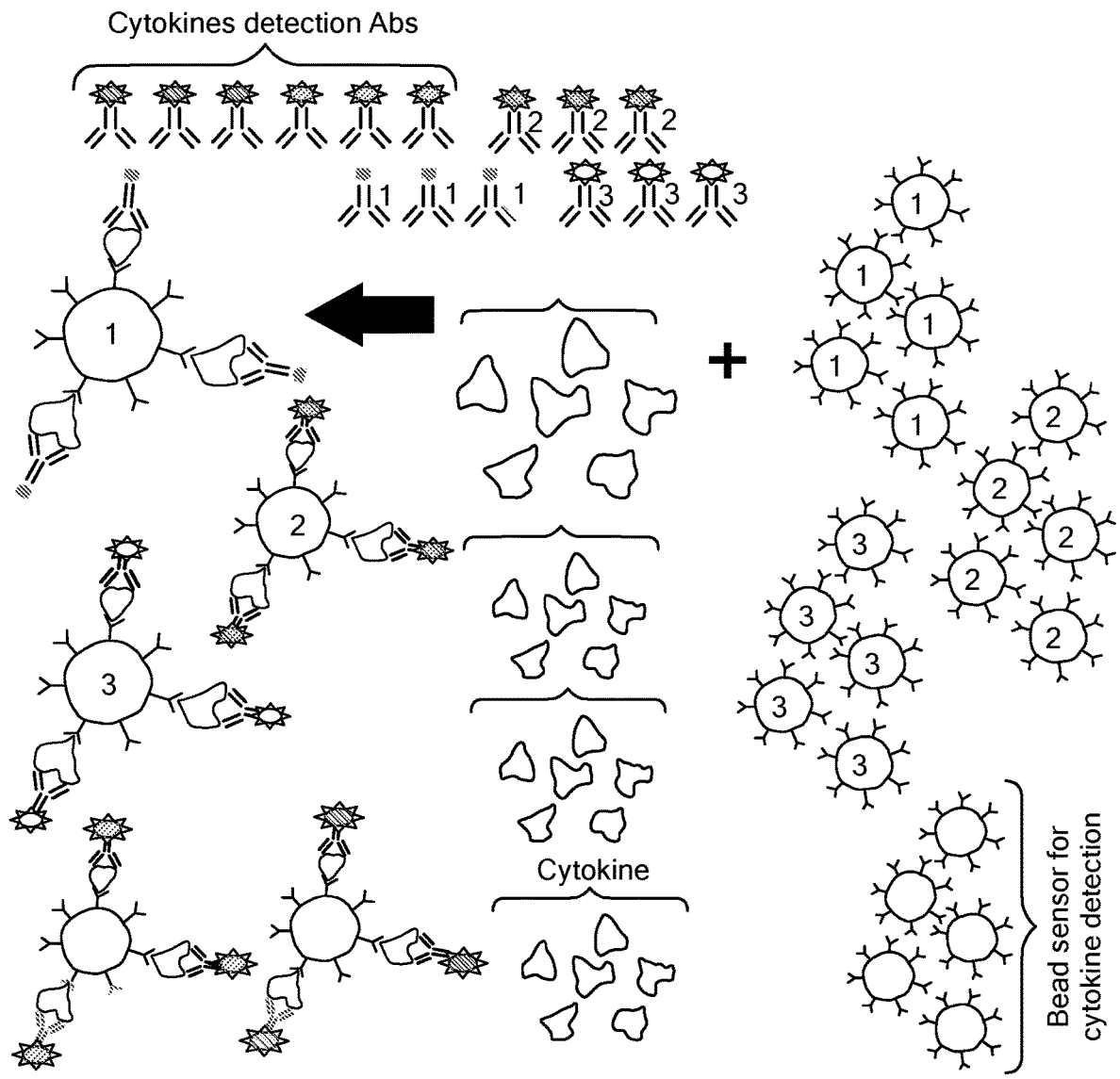
FIG. 2 shows a schematic illustration for multiplex detection of bacteria using bead-based immunoassay for capture of *E. coli, Klebsiella pneumoniae, Enterobacter* species, *Pseudomonas aeruginosa*, and *Proteus* as well as for cytokines.

In the present protocol, the identification of bacteria in a urine sample includes two major steps: 1) the capture of target bacteria from the sample, and 2) the identification of the captured bacteria via association with a bar-coded microbead. In addition, bead-based detection of inflammatory cytokines such as IL-6 and IL-8 present in urine samples of infected patients is employed. An example strategy is illustrated in FIG. 2. In this protocol, focus is on development of bead-based detection for the following Gram negative bacteria: *E. coli*, *Klebsiella pneumoniae*, *Enterobacter* species, *Pseudomonas aeruginosa*, and *Proteus*, and for IL-6 and IL-8. Capturing antibodies are biotinylated with EZ-Link NHS-PEG4-Biotin (Thermo Scientific, USA) according to the manufacturer's protocol and are diluted to a final concentration of 0.5 mg/ml in PBS with 0.005% (v/v) Tween-20 (Sigma, USA). The purified antibody is applied to streptavidin conjugated polystyrene microspheres (Spherotech) at a ratio of 20 µg of IgG per mg particles. The microcentrifuge tube containing the mixture is shaken at RT for 90 min. Unbound active sites of the bead are blocked with BlockAid (B-10710, Invitrogen, USA) for one hour. Finally, the microspheres are washed in PBS (Sigma, USA) with 0.5% (w/v) BSA (Sigma, USA), diluted to a final concentration of 0.5 mg/ml, and stored at 4° C. Detection antibodies are labeled with Alexa Fluor 488 (Invitrogen, USA) according to the manufacturer's protocol.

Commercially available antibodies are available for each species (and/or can be developed) and may be investigated as described below for performance characteristics. For example, for preparation of bead capture of *Klebsiella pneumoniae*, avidinylated beads may be conjugated to biotinylated anti-*K. pneumoniae* antibodies (ab20947 Abcam) and detected with FITC-conjugated rabbit polyclonal antibody to *Klebsiella* (LS-C103383 LS Bio Inc); for capture of *Enterobacter cloacae*, avidinylated beads are conjugated to biotinylated anti-*E. cloacae* antibody (ab36931 Abcam) and detected with FITC-conjugated mouse monoclonal antibody to *Enterobacter cloacae* (GTX41313GeneTex); for *Pseudomonas aeruginosa* capture, avidinylated beads are conjugated to biotinylated anti-*Pseudomonas aeruginosa* antibodies (PA1-73116 Thermo Scientific (Pierce Biotech antibody) and detected with FITC-conjugated rabbit polyclonal antibody to *P. aeruginosa* (PA1-73117 Thermo Scientific (Pierce Biotech antibody); etc. Beads for detection of specific bacterial species are chemically bar-coded for individual identification.

Figures 3A, 3B:
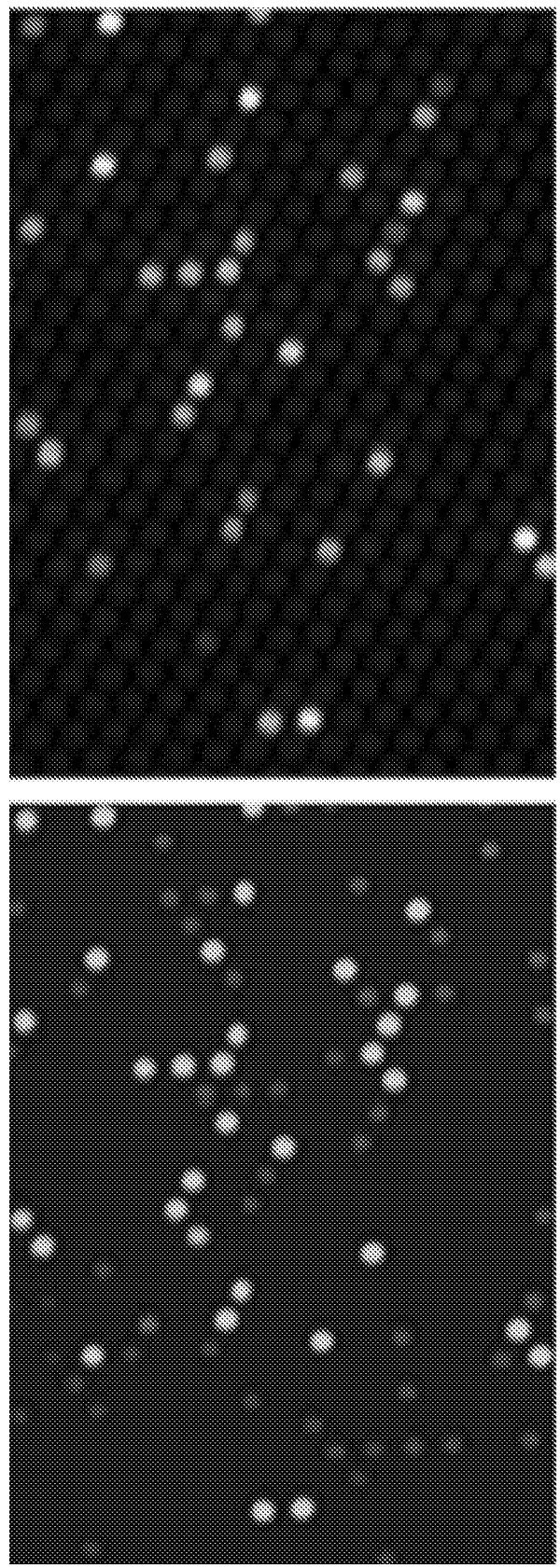
FIG. 3A shows two fluorescently distinct beads encoded with different concentration of Eu (0.1M for dimmer and 1M for the brighter bead).
FIG. 3B shows the detection of one of the analytes with secondary antibodies conjugated to FITC captured only on the 1M Eu bead.

Previously developed bar-coded multiplex microsphere arrays in which the microspheres are functionalized with different antibody probes may be employed (FIGS. 3A-3B). Beads are pre-labeled within different Europium concentrations, allowing them be clearly differentiated via their fluorescent characteristics. Specifically, in an embodiment, each bead may be created with a distinct spectral characteristic for each target bacterial species of interest. Distinct beads can be constructed that allow for simultaneously distinguishing >10 analytes by this method. Microspheres may be prepared from 50 µL (5 mg) aliquots of a 5 µm avidin-functionalized microsphere stock. The aliquots will be washed in triplicate with 200 µL of PBS and then be washed in triplicate with 200 µL of THF. A 200 µL solution of 0.1M Europium (Eu)-dye (e.g., $EuF_2$) in THF may then added, and the microsphere suspension is then shaken in the dark for 2 h at room temperature (RT). The reaction vessel may then be centrifuged, and the microsphere pellet washed six times with 200 µL of MeOH and then washed six times with 300 µL of PBS (0.154 M NaCl, 2.7 mM KCl, 10 mM sodium phosphate, and 1.7 mM potassium phosphate, pH 7.4). The encoded microspheres may then be suspended in 500 µL of PBS with 0.01% Tween-20 and stored at 4° C. in the dark. An identical procedure may be followed for additional sets of microspheres; however, the europium dye concentration in THF solution may be incrementally increased up to 1 M. To illustrate, FIG. 3A shows two fluorescently distinct beads encoded with different concentrations of Eu (0.1M for dimer and 1M for the brighter bead). In turn, each bead is conjugated to different capturing antibodies, thus allowing different analytes to be distinguished, despite using the same conjugated fluorophore (FITC) on detection antibodies. FIG. 3B demonstrates the detection with secondary antibodies conjugated to FITC of one analyte which was captured only on the 1M Eu bead.

Though the success of bead based immunoassays depends on the identification of high specificity antibodies to the multiple pathogens, commercially available antibodies have demonstrated adequate specificity. Use of distinct antibodies for capture and detection allows additional tuning of specificity. Furthermore, if necessary, embodiments may utilize custom recombinant antibody services to generate specific panels of pathogen recognition antibodies with AxioMx services. In addition, an embodiment may be directed to both rat and mouse hybridoma development options for producing custom monoclonal antibodies to synthesize surface exposed common genus or species antigen epitopes with Thermo Scientific Pierce Custom Antibody Services (e.g., Enterobacterial common antigen (55,56), *Klebsiella* genus core LPS epitope (57), *Pseudomonas* Psl58, etc.

Integration of the Bead-Based Assay and Validation for Bacterial Detection

To detect bacteria, microsphere-based assay components developed above may be employed. Several lines of experiments may be used during bead development. Specifically, the properties of specific antibodies may be examined for both capture and specific detection of bacteria. Initial experiments may be performed in liquid solution and performance characteristics of reagents determined by both fluorescent microscopy and automated plate-based BD FACSArray™ bioanalyzer, BD FACS™ readout. Both methods have been optimal for bead-based assay development in the past. (50-54) For microscopy, a Zeiss 200 Axiovert microscope and AxioCAM MRm digital camera setup already established in a laboratory may be used. Image processing and analysis may be conducted using ImageJ software or the like. Fluorescence emissions may be collected with a set of filters (535-540 nm, 617-673 nm, 710-740 nm; Semrock) and photomultiplier tubes (Hamamatsu). Fluorescence detection may be driven at 100 kHz by a custom data-acquisition system (Labview; National Instruments) that also allows signal processing and statistical analysis.

Detection of bacteria of interest at various ratios to beads may be examined in appropriate matrix (urine) admixed with diluents that will be used during drop formation to replicate conditions in the device described in Example 2. Embodiments are designed to consistently and specifically detect one bacterium per bead, which following the Poisson distribution, should mean achieving consistent detection at bacteria to bead ratios of <1:10. The quantitative aspects of signal (signal per bead×number of beads positive) may be assessed through 10-fold dilution series to establish a linear range of the assay.

In specificity studies, bead sensors may be tested to determine whether they cross react with Gram-positive and Gram-negative organisms that potentially can be found in urine. If either reactivity or cross reactivity is found wanting, alternative antibodies, combinations of antibodies, or different ratios of antibodies may be examined either for capture or detection. Furthermore, to improve analytical specificity, if necessary, a strategy of using different antibodies for capture and detection may be considered, thereby improving on the specificity of the two antibodies individually. Specificity may be in line with other detection methods such as MALDI-TOF and commercially available biochemical panels where an identification at the species level is generally acceptable if with >95% confidence, with no tolerance for error out of the bacterial familial level. A test of a minimum of 50 isolates for each species may be used to establish sensitivity/detection and 100 isolates from other diverse species to establish specificity of each iteration of bead format. Inter-assay reproducibility goal is >95% at the LOD and 100×LOD in spiked matrix. The ability to find specific antibodies that might potentially be problematic for a given species and significant effort may need to be employed, mitigated potentially by the fact that treatment and susceptibility cutoffs for all Enterobacteriaceae is essentially the same. Lastly, co-detection using different ratios of species of interest may be used.

Example 2: Development of System for Differential Diagnosis and Antimicrobial Susceptibility Testing In this example, disclosed is a fully integrated droplet based microfluidic device to detect and establish antimicrobial susceptibility within intact droplets is disclosed. The technology developed herein includes: 1) bead sensors and detection assay reagents as well as urine sample co-encapsulation to generate droplet based microreactors for detection, 2) droplet microarray technology to analyze the captured bacteria and 3) droplet merging technology for timely delivery of antimicrobials for susceptibility testing.

Microbead-Based Assay Using IL-6 and IL-8 Cytokine Interrogation

Figure 4A:
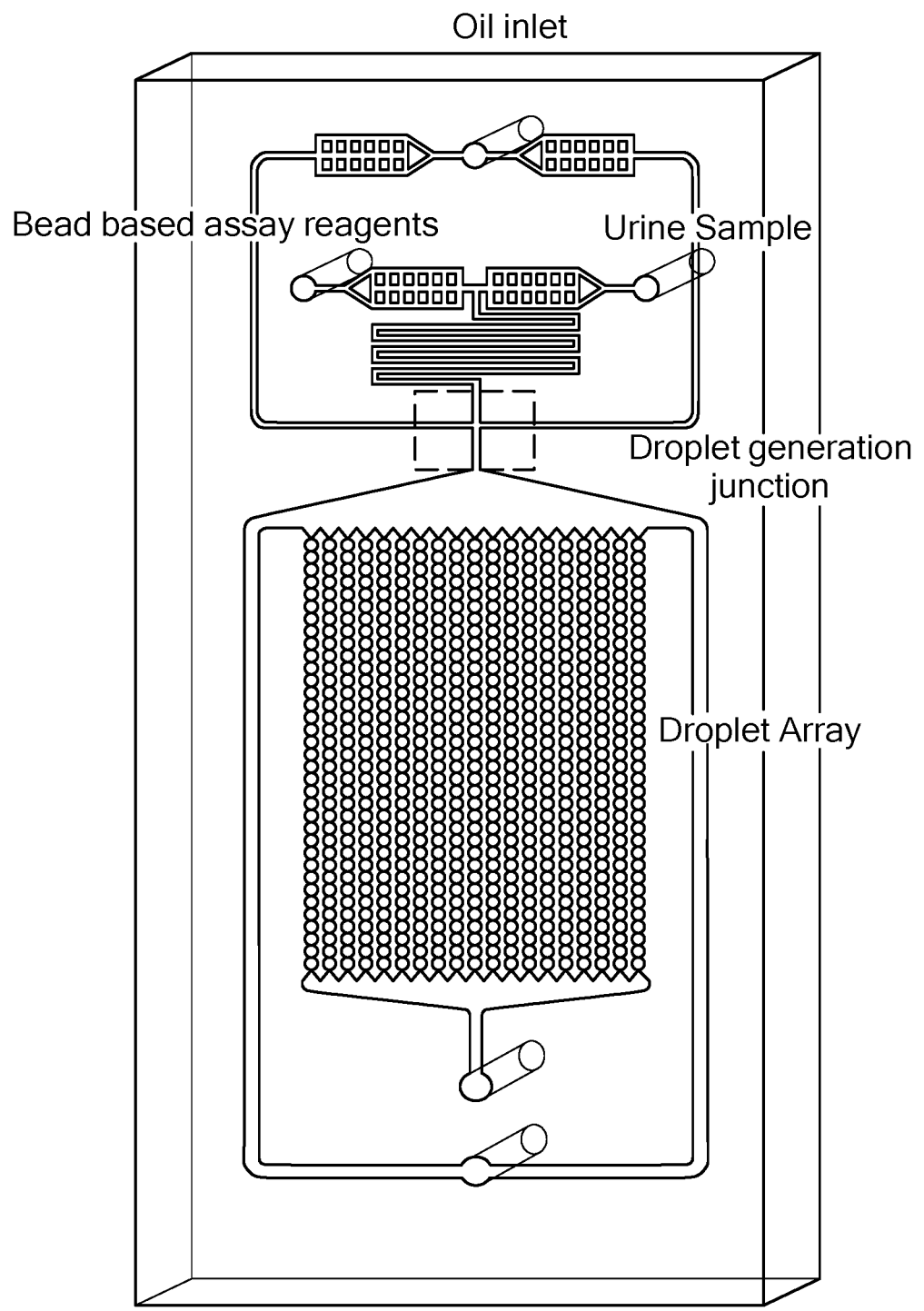
FIGS. 4A-4C show a polydimethylsiloxane (PDMS) microfluidic chip generated using standard soft lithography methods, combining functionalities of droplet generation and an incubation chamber array of 1000 droplets.
Figure 4B:
Figure 4B:
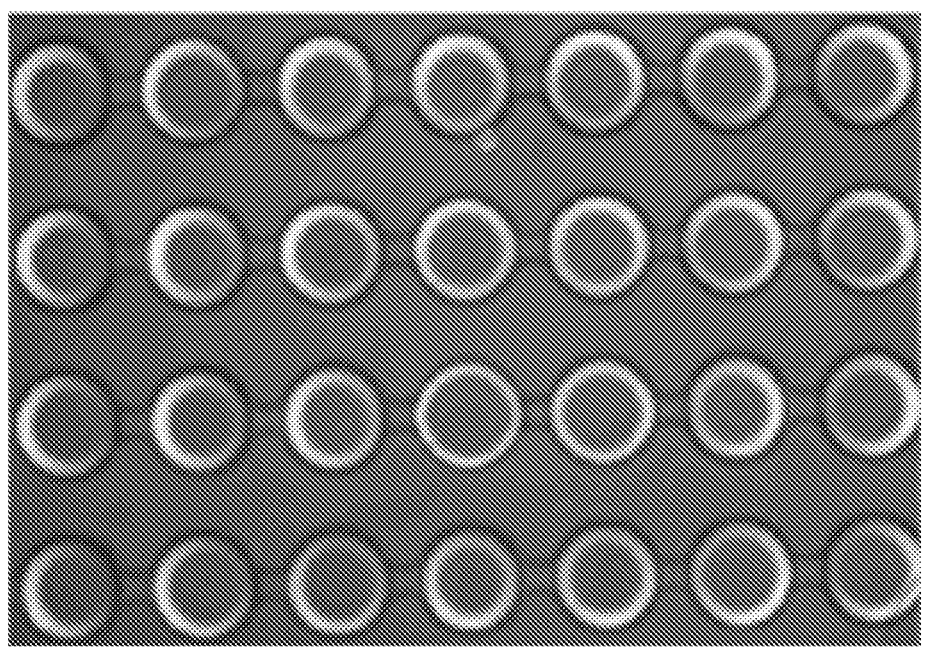
Figure 4C:
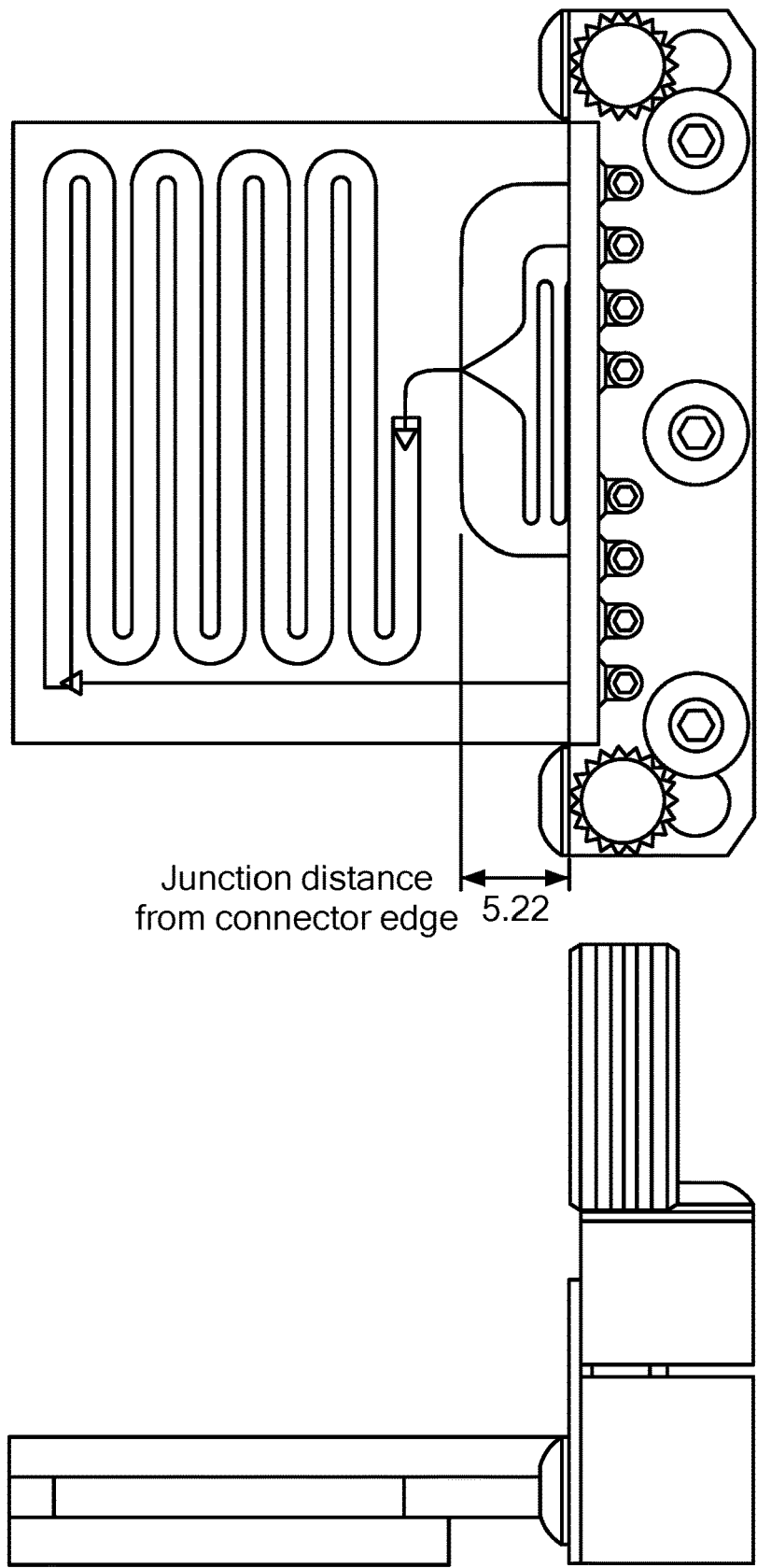
Figure 5:
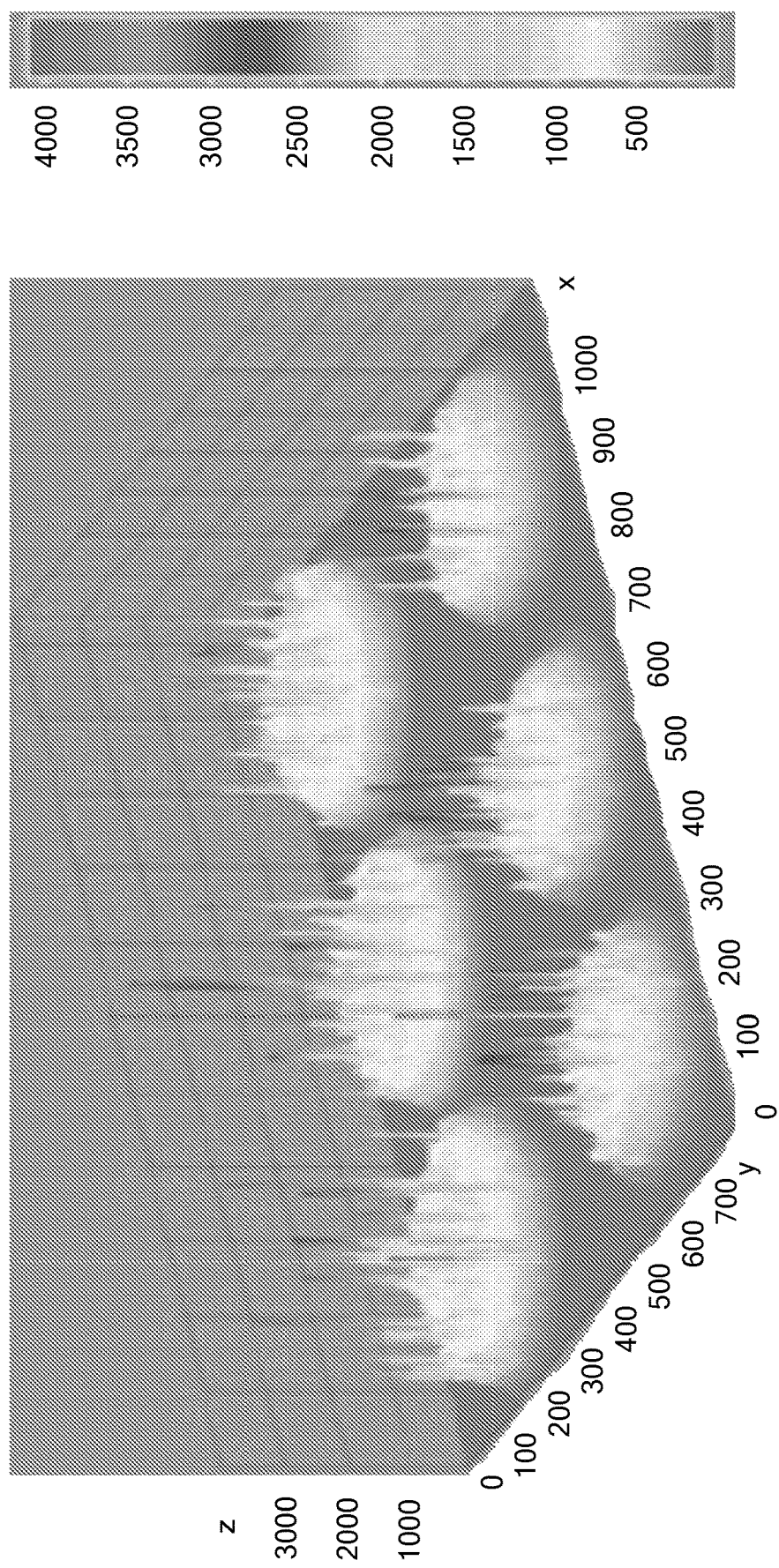
FIG. 5 shows the fluorescence intensity of the microbead after capturing the analyte. Each spike represents a bead, and its fluorescence is proportional to the number of bacteria bound.

Two chips disclosed below are designed with variations on geometry to meet the single bacteria interrogation and co-encapsulation with assay reagents and antimicrobial agent requirements. The first design presents a simpler approach, where the polydimethylsiloxane (PDMS) chip is generated using standard soft lithography methods, combining functionalities of droplet generation and an incubation chamber array of 1000 droplets (FIGS. 4A-4C). The generation of monodisperse droplets is conducted in a microchannel through shearing flow at a flow-focusing zone that is illustrated in FIGS. 4A-4C. Three perpendicular inlet channels form a nozzle. The individual syringe pumps are used to control flow rates of the central stream of the oil phase and the stream of sera sample and the bioassay reagents (microsphere sensors and detection antibodies) (FIG. 5). The channels are coated with Aquapel (PPG Industries), and the flow rates are controlled by syringe pumps (Harvard Apparatus). To form droplets, the flow rate ratio of water to oil may be adjusted to the Qw/Qo=0.5 (Qw=1 µL/min and Qo=2 µL/min). The generated droplet volume is ~1.8 nL corresponding to a spherical droplet diameter of 150 µm. This chip is ideal for optimizing conditions for bacterial capture, flow rates, etc. Once initial functional determinations are made with a system that can be rapidly re-configured as necessary for optimization and at relatively low cost, a mechanically more robust PDMS/glass chip may be used that has the requisite characteristics for inclusion in a diagnostic device. The chip also may be composed of both robust glass for droplet generation and gas permeable PDMS incubation for cell interrogation in droplets. This microdroplet system enables rapid droplet generation to produce more than 10,000 monodispersed droplets per second ranging from 5 µm to 250 µm in diameter. The flow rates in this device may be controlled by Mitos pressure pumps that provide a pulseless liquid flow which is ideal for applications where a highly stable flow is required, such as droplet formation. In this device, bead based sensors and urine sample are co-encapsulated in droplets that are formed at a T-junction as described in FIG. 4A. These droplets then enter the PDMS incubation part of the chip (FIG. 4D). To generate the PDMS part of the device, the PDMS layer may be bonded to the glass chip with serpentine geometry for cell incubation. This PDMS based incubation part of the chip allows appropriate gas exchange to maintain live co-encapsulated bacterial cells in microreactor droplets during interrogation.

The limit of detection in spiked samples for the device format may be determined. The device is validated for detection of clinically-relevant (1000 to >100000 CFU/ml) levels of organisms found in UTI patients. As it is possible that low levels of bacteria (<1000 CFU/ml) may be present in patients without symptomatic infection, or present as colonizing organisms in patients with other pathogens, the fluorescence intensity may be specifically calculated to identify clinically relevant quantities of bacteria (i.e., 1000 CFU/ml). Determinations may be made whether spiked pathogens of interest can be detected and to what degree (10-fold serial dilutions) with a goal of detecting 1000 to 100000 CFU/ml within a 30 minute time frame.

In some embodiments, the analysis performed in Example 1 may be repeated within the ScanDrop system to determine LOD, quantitative linear detection range, and specificity for pathogens of interest, realizing that the compartmentalization in nanodrop format might change binding characteristics of antibody or FISH probes and efficiency of microscopic readout. Therefore accuracy and especially sensitivity may need to be re-established in this alternative format. In some embodiments, quantitative performance may be optimized via quantitative image analysis (See FIG. 5, bead number positive×signal strength=quantity of bacteria per volume analyzed), developing robust calibration curves for each reagent bead assay through serial dilution studies. In some embodiments, performance characteristics of bead capture-based cytokine sandwich assays may be similarly incorporated and examined confirming ability to specifically detect and quantitate physiological cytokine concentrations.

Fluorescence Detection and Droplet Sorting Subsystem

Figure 6A:
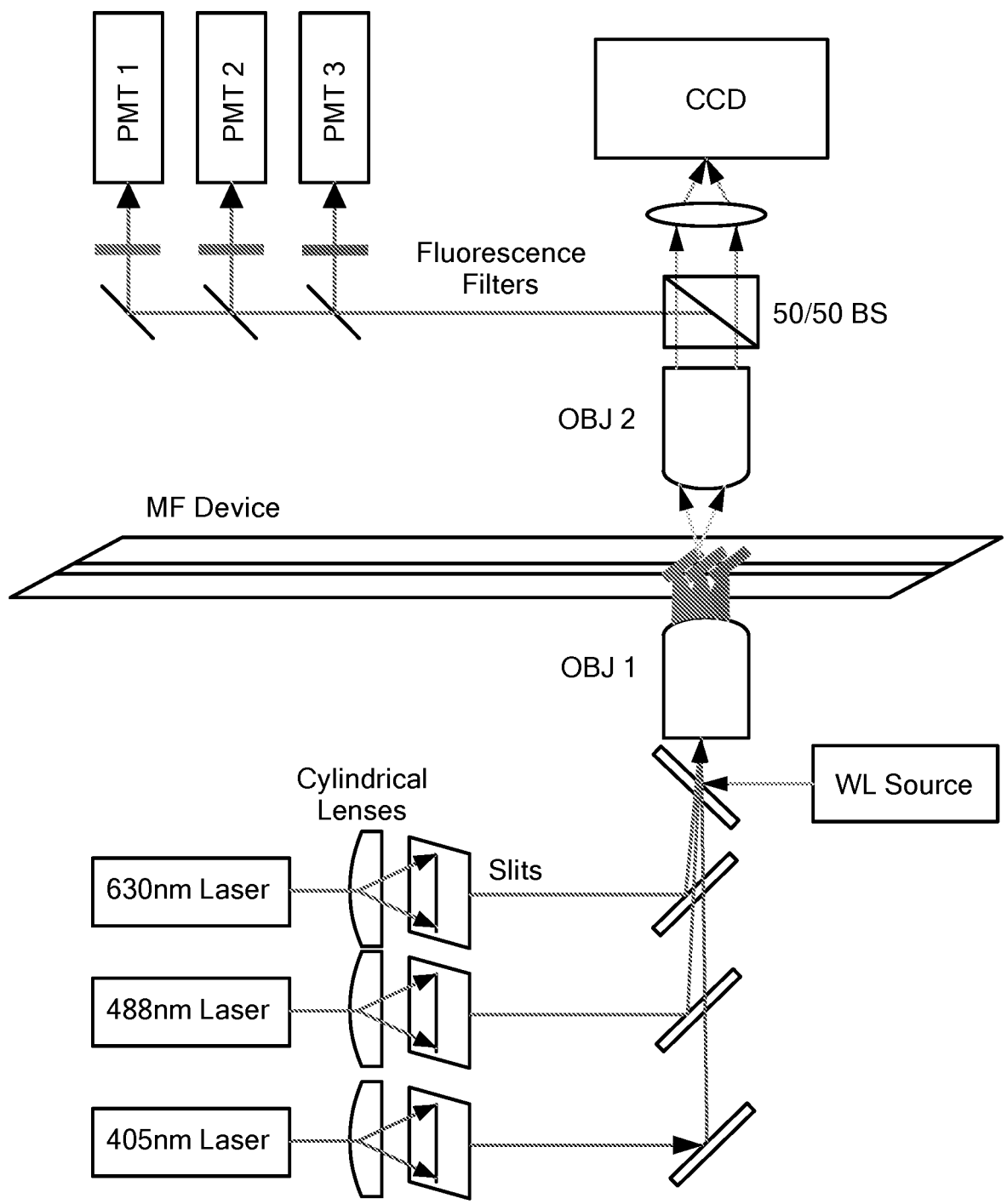
FIG. 6A shows a schematic illustration of the fluorescence detection and white light alignment system. Laser-filter combinations are chosen to allow multiplexed detection of up to 3 distinct fluorochromes.
Figure 6B:
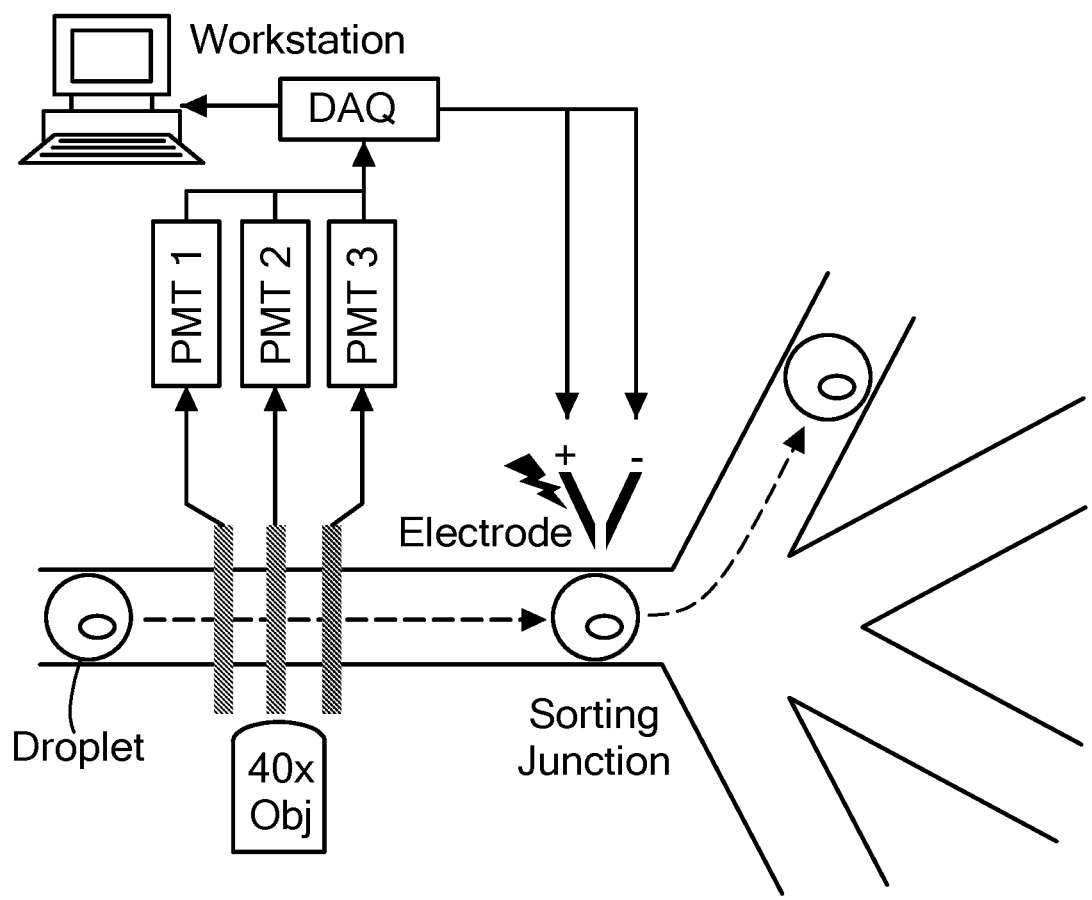
FIG. 6B shows how droplets can be sorted using dielectrophoresis and based on the measured fluorescence signal minimal cross-talk between channels. Beams can be expanded with cylindrical lenses and then focused to a slit though a 60× microscope objective at different positions along the channel.

To allow isolation and further manipulation of the detected bacteria in the droplet for rapid susceptibility testing, a FADS microfluidic device for droplet sorting can be used. The FADS may be fabricated along the incubation channel of the device described in FIGS. 4A-4D. An additional inlet channel may be designed to introduce oil into the end of incubation channel to space the droplets. Thus the incubation channel will be followed by a sorting-shaped junction where droplets are actively sorted via dielectrophoresis (FIG. 6). Droplets may be automatically sorted at the outlet based on detection of up to 3 distinct fluorescent markers. These may be exemplified by DAPI (blue), FITC (green) or Cy5 (red), which are chemically stable, spectrally well-separated dyes. The schematic of the reader-sorter subsystem is shown in FIG. 6. The channel may be illuminated simultaneously with up to 3 laser slits. As droplets pass single-file through the field-of-view, fluorescent signals may be detected with a bank of PMTs, and droplets may be guided into 1 of 4 outlet channels using dielectrophoresis (i.e. the three fluorophores plus an un-labeled droplet channel). Major subsystem components are described as follows:

Excitation Lasers: Up to 3 solid-state diode lasers (Crystalaser Inc.) may be focused in slits across the microfluidic channel corresponding to the excitation wavelengths of the three fluorophores (405 nm, 488 nm and 633 nm). In combination with the fluorescence detection filters, these are selected to be well spectrally separated to allow multiplexed detection.

Photomultiplier Tubes (PMTs): A set of 3 PMTs may be used to detect the fluorescent signal from labeled droplets. Fluorescent light may be collected with a second 60× microscope objective, split into 3 detection channels with 50-50 beam-splitters, and then filtered with appropriate band-pass filters corresponding to each fluorophore (centered at: 450 nm, 550 nm, and 680 nm). The output of each PMT may be pre-amplified and then acquired with a multifunction data acquisition board (National Instruments) connected to a personal computer. Software running on the PC allows real-time detection of fluorescent spikes on each of the 3 detector channels. That the laser and filter combinations can be adjusted to allow flexible operation with other fluorophores as needed.

Sorting Junction: After passing through the laser slits, droplets may be diverted into collection outlets using dielectrophoresis. A micro-electrode may be deposited next to the channel at the sorting junction during fabricated and connected to a high voltage, programmable power supply (Stanford Research Systems). Software written in Matlab may be used to control the magnitude of and frequency the applied AC voltage applied across the electrode on the basis of droplet fluorescent signature, thereby controlling the magnitude of deflection and outlet channel. The amplitude of the AC potential may be selected to be as small as possible to minimize the possibility of shearing the droplets.

Alignment Optics: A white-light source and monochrome CCD camera may be employed to allow alignment of the microfluidic chip on the subsystem, and in particular to align orthogonal illumination of the flow channel with the 3 laser slits and detection optics.

Figure 7B:
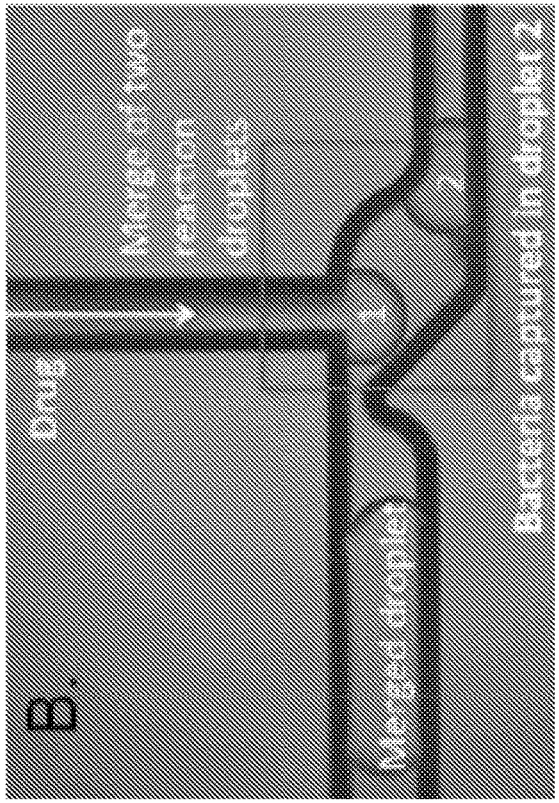
FIGS. 7A and 7B show droplet merging technology incorporation into the microfluidic platform device.
Figure 7A:
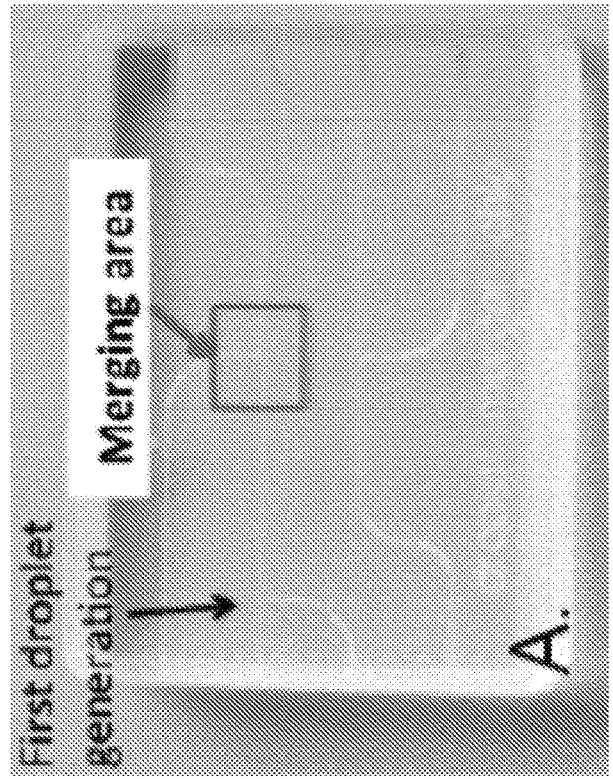
Figure 7C:
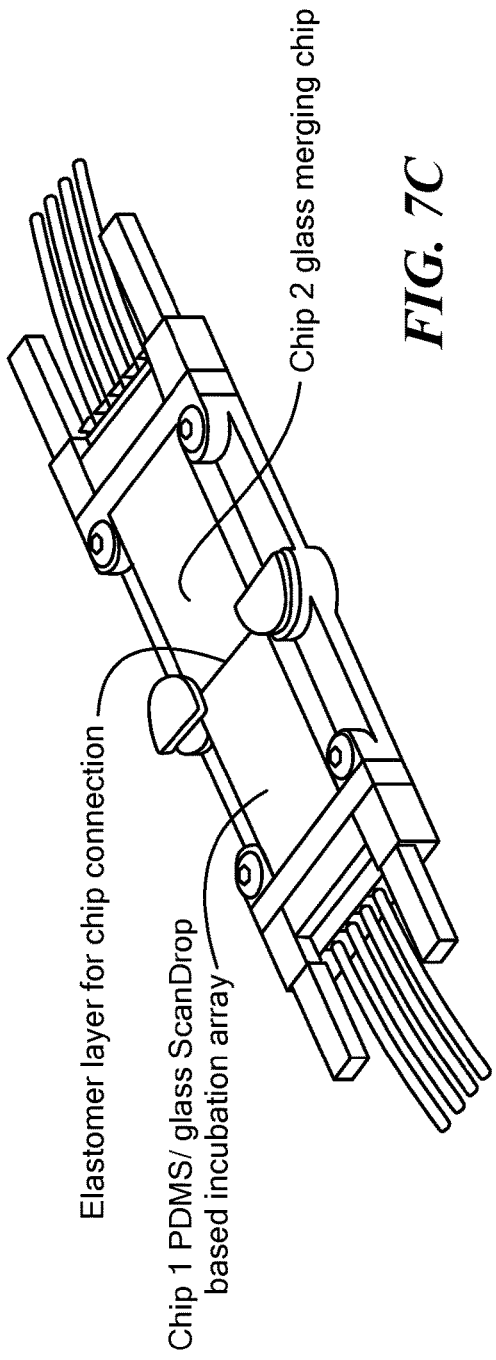
FIG. 7C shows a PDMS glass chip interface that allows creating fast and reliable fluidic connections to PDMS-on-glass devices from glass based devices.

Use of Droplet Merging Technology for Controlled Delivery of Antimicrobials for Rapid Antimicrobial Susceptibility Testing Herein, a glass microfluidic chip is disclosed that facilitates fast and consistent merging of two individual droplet streams (see FIGS. 7A and 7B), benefiting a wide range of applications, including delivery of antimicrobials and bioassay reagents to perform high throughput susceptibility testing. Unlike other methods that incorporate expensive and bulky high voltage electronics to merge droplets using electrostatic forces, this chip feature works by simply "squeezing" droplets together in a carefully designed merging chamber (FIG. 7B). The merger chip forms droplets with cells at a T-junction. These droplets then enter the droplet merging geometry, combining droplet containing cells with a secondary reagent such as an antimicrobial agent. A "droplet merger chip" or feature may be is designed for the merging of droplets in the volume range 400 pL (90 µm) to 900 pL (120 µm). Since the example embodiment device is made out of glass, it has an excellent chemical compatibility and high visibility (excellent access for optics). It is not toxic to cells (compared to chemical fusion), does not required specialized equipment, and is inexpensive (compared to electrofusion). Importantly, the fused droplets remain confined within the array and can be monitored in fixed positions during an extended incubation. In addition, the generated merged droplets can be collected or introduced into previously described PDMS based array device for interrogation.

Figure 8A:
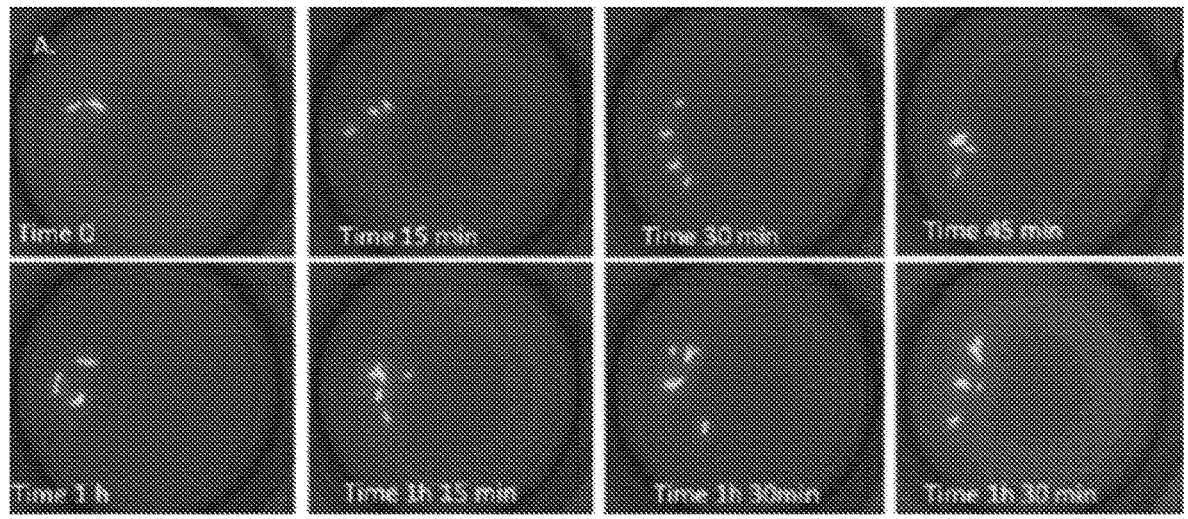
FIG. 8A shows replication of bacteria in droplet over the course of time.

The merger chip technology may be employed for incorporation of antimicrobials for susceptibility testing in combination with live/dead staining reagents. See FIG. 8. After capturing bacteria on the bead surface, the merger chip may be used to test how antimicrobials affect the growth and viability of captured bacteria. For susceptibility testing, embodiments may include merging antibiotics dissolved in Mueller-Hinton broth, and pre-incubation for 2 hours to allow several doublings to occur, and for antimicrobial static/cidal effects to manifest. Susceptibility can therefore be simply measured by counting bacteria and observing replication inhibition (FIG. 8). However, merging technology also allows incorporation of non-toxic, dead-cell fluorescent staining dyes (SYTOX Green, Orange, Blue etc. (63)), which may increase specificity by providing a separate growth-independent measure of cell viability. Specifically, live cells have intact membranes and are impermeable to dyes such as SYTOX Green, which only leaks into cells with compromised membranes. Therefore, inclusion of a dead cell stain provides a rapid and reliable method for discriminating live and dead bacteria. Importantly, as the system is dynamic, permitting growth, bactericidal differences between susceptible and resistant populations may be amplified during the incubation period.

Antibiotics of interest may be trialed at multiple doubling dilutions. Time-growth-kill kinetics may have to be determined empirically and correlated with MIC data to determine optimal predictive concentration for each antimicrobial of interest for assignment of susceptible, intermediate, and resistant (CLSI) categorization. Similar correlation analysis has been applied previously in clinical systems such as the automated Vitek (Biomerieux) and microscope-based Accelerate Diagnostics64 susceptibility testing systems to extrapolate MIC, and standardly for determination of disc diffusion zone cutoffs. In some embodiments, performance characteristics may be established for several antibiotics of importance for treatment of GNB and last lines of therapy for MDR GNB, specifically nitrofurantoin, fosfomycin, trimethoprim-sulfamethoxazole (first-line agents); and ciprofloxacin, ceftazadime, cefepime, meropenem, piperacillin/tazobactam, and amikacin (MDR GNB agents).

Figure 8B:
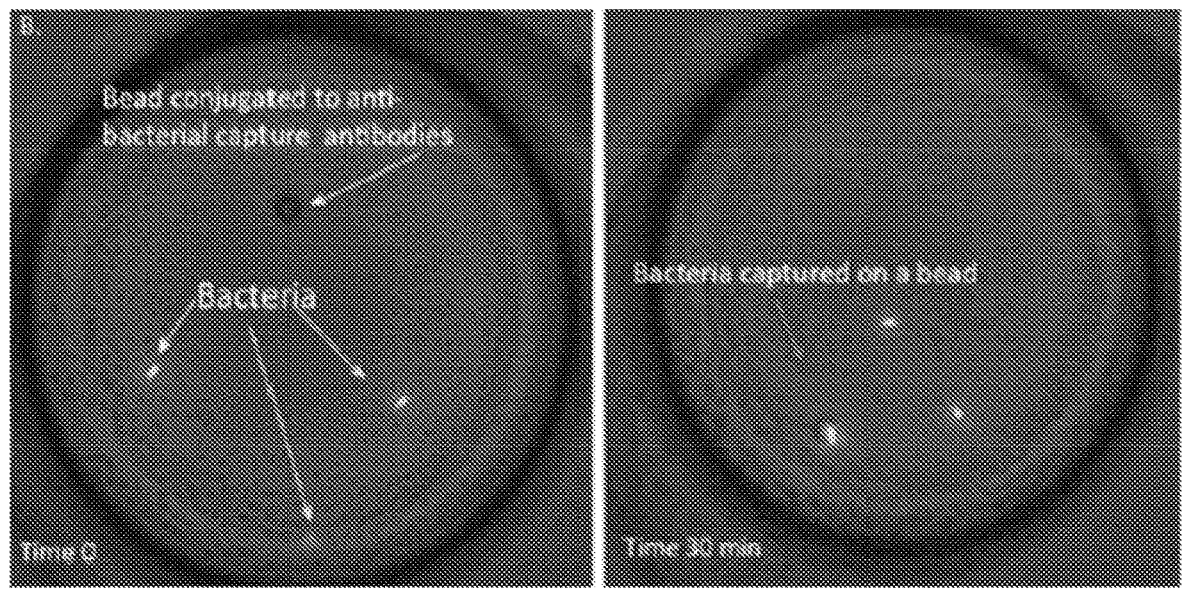
FIG. 8B shows capturing single bacteria on a bead sensor. Note, in this panel, only one bead was present in the droplet which allowed single bacteria capturing to a bead.
Figure 8C:
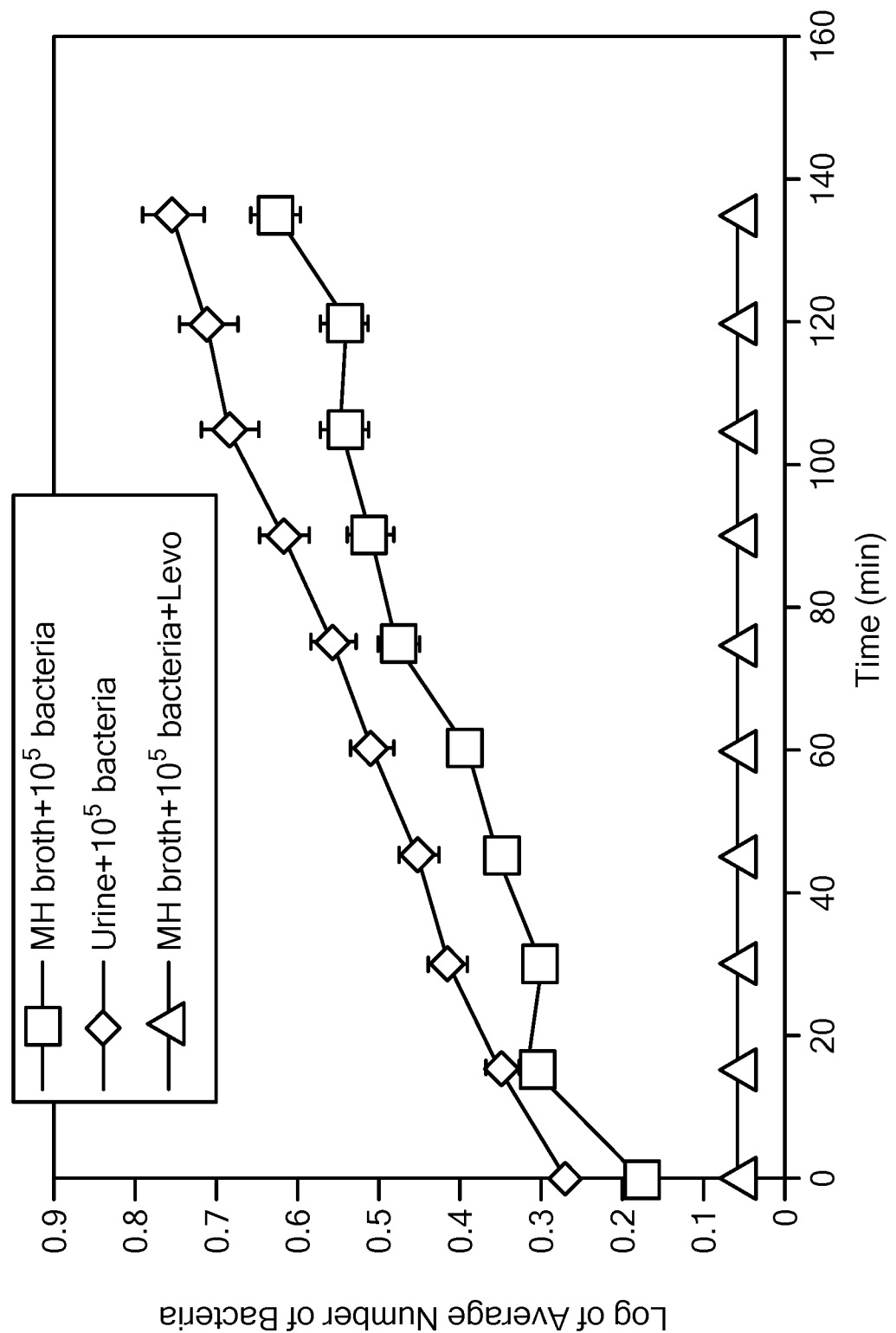
FIG. 8C shows bacterial intradroplet growth with and without levofloxacin at 1 mg/L.
Figure 9A:
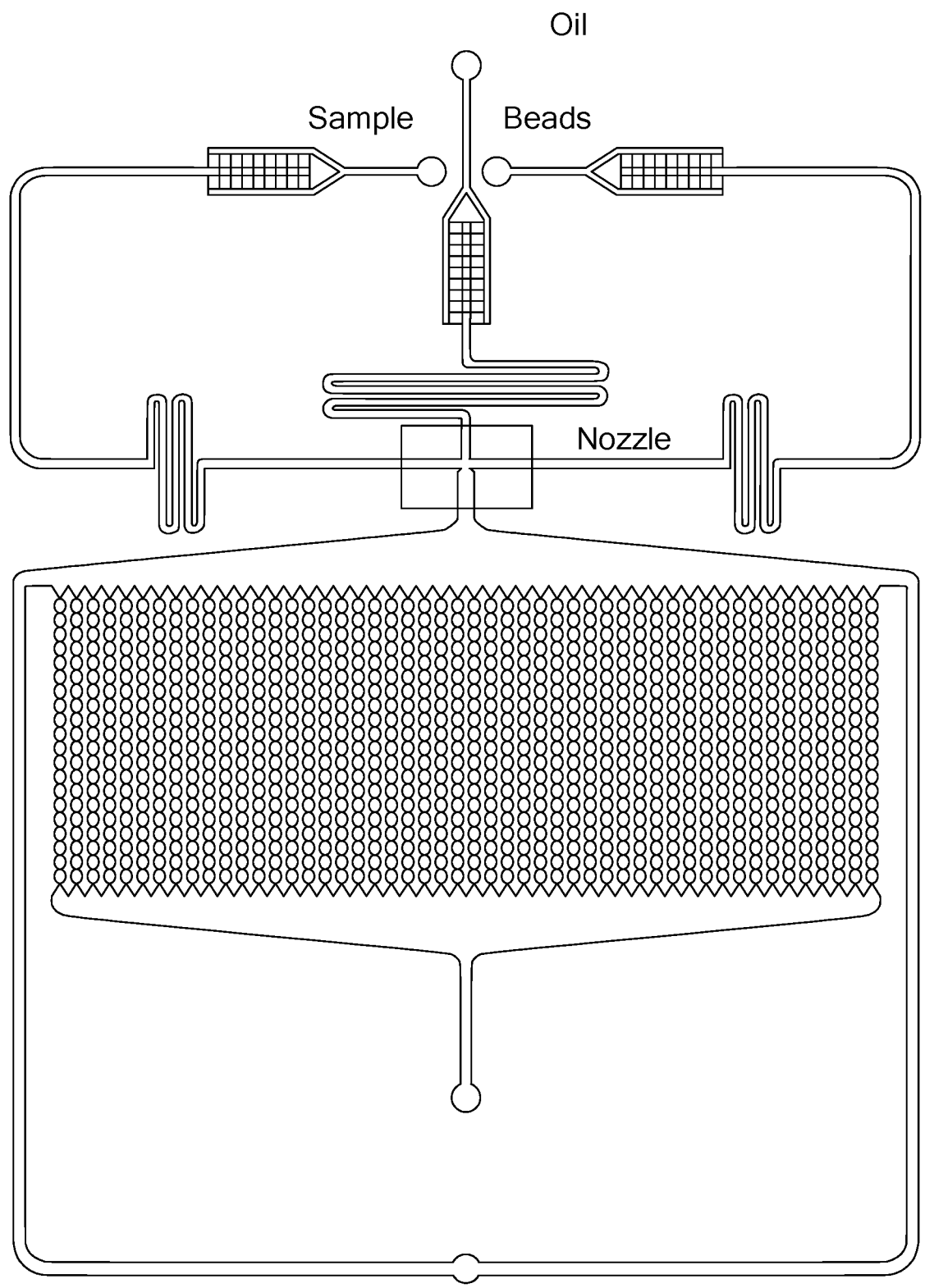
FIG. 9A is a schematic representation of a prior art device for forming aqueous microdroplets in oil, the microdroplets containing a mixture of a liquid sample and a suspension of microbeads. The microdroplets are distributed into the droplet array in the lower half of the figure.
Figure 9B:
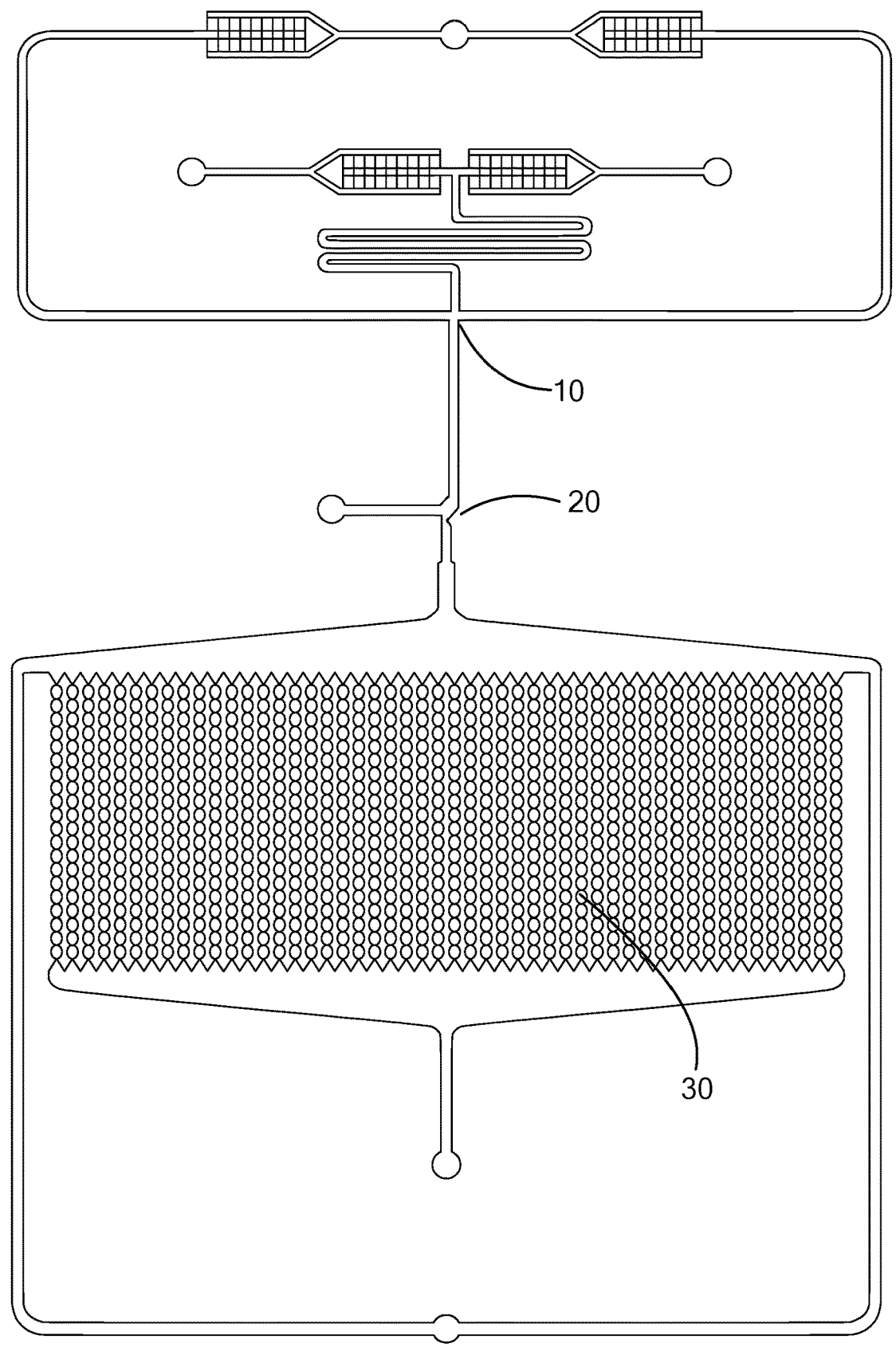
FIG. 9B shows a device according to the present invention, in which a droplet merging junction 20 for adding a reagent to preformed microdroplets prior to incubation has been added between the upper half, after droplet forming junction 10 and before microdroplet array 30.

Encapsulation and detection of clinically relevant concentrations (1000 to >100000 CFU/ml) of green fluorescent protein (GFP) $E.$ $coli$ K-12 directly from urine matrix have been demonstrated without need for any prior concentration steps. As it can be seen in FIG. 8A, replication of bacteria, several doublings of numbers, within single droplets were demonstrated from t=0 to t=1.5 hrs, enabling direct assessment of the susceptibility to antibiotics such as levofloxacin (no replication) based on their growth/replication inhibitor effects. Bacteria in FIGS. 8A-8C were treated in urine. Next, in some embodiments, the capturing of a single bacterium on a single bead previously functionalized with capturing anti-bacterial antibodies was monitored. As can be seen in FIG. 8B, the bacterium attachment was demonstrated only after 30 min of incubation. Bigger sized beads (18 µm) may be specifically functionalized with anti-bacterial antibodies to allow more than one bacterium to attach to a single bead surface. The droplet based culture approach allows physical and chemical isolation of droplet cultures thus eliminating the risk of cross-contamination. The fast and efficient mixing of reagents and gases that occurs inside droplets allows capturing and detecting the bacteria in a fast manner. In addition, demonstrated herein is the ability to incubate stable droplets in the proposed droplet array at 37° C. for bacterial replication on a bead. Later, the droplets which contain the detected bacteria at a very high-throughput may be sorted and antimicrobials added for rapid susceptibility testing utilizing droplet merging chip technology.

Example 3: Diagnostic Validation

The use of a microfluidic system for bacterial detection and quantification of select pathogens in patient clinical samples and associated IL-6/IL-8 cytokine levels is exemplified.

Clinical urine culture samples are collected in urine transport tubes that stabilize uropathogen numbers and viability, and urine samples are stored at 4° C. immediately after specimens are cultured and are therefore available for later analysis. Retrieved urine samples may be tested and correlated with clinical reports and parallel determination of CFU/mL of specific organisms. Clinically, urine cultures are plated using calibrated loops and results reported out quantitatively in log 10 concentration. More specifically, for clinical reporting, urine culture results are divided into four quantitative categories: no growth, <10,000, 10-100,000, and >100,000 CFU/ml. Isolates are also speciated by the Vitek 2 (Biomerieux) automated identification system. Biotype numbers (a numerical summary of biochemical reactions) are determined for each isolate and identify potentially unique strain subtypes.

Example 4: Killing of Tumor Cells by Dendritic Cell-Activated T Cells

The functional responses of activated effector immune cells were investigated by utilizing the microfluidic droplet generation and docking array platform of the present invention. Anti-tumor immune responses of NK cells and T lymphocytes stimulated by interaction with mature dendritic cells (DCs) were investigated. While NK cells are known to target cancer cells non-specifically (i.e., without previous antigenic exposure), T cells require maturation signals from cognate DCs prior to target cell killing. By co-encapsulating individual mature DCs, naïve T cells and cancer cells within a droplet, efficiency of DC-based vaccines against cancer cells can be tested.

Immunological synapse formation was investigated between T cells and DCs pre-exposed to cancer cell lysate. The activated T cells then mediated the death of co-encapsulated cancer cells. The rapid reaction kinetics in droplet microfluidics facilitated cell-cell interaction and delivery of cytotoxic hits to cancer cells within two hours in this integrated platform. The microfluidic droplets also allowed determination of strong heterogeneity during immune synapse formation with respect to transient vs. stable interactions and the duration of T-DC conjugate formation. Serial brief encounters were observed between the same DC-T cell pair, which would not be possible with microwells or hydrodynamic cell traps. Further detected were contact dependent cancer cell lysis by NK cells, and quantified heterogeneous profiles of cell conjugation, delivery of lytic hits and target death. It was observed showed that a single NK cell resulted in multiple cell deaths, sometimes interacting with up to four target cells simultaneously. NK-mediated target cell lysis in the presence of anti-PD-L1 blocking antibody was also characterized, as the PD-1/PD-L1 axis is involved in promoting immune escape in a number of solid and liquid tumors. Humanized antibodies against PD-1 and PD-L1 are presently utilized in clinical trials and have shown great promise in antitumor immunotherapeutic treatments. In droplets, 50% single target cell lysis was observed in significantly shorter duration compared to control. Taken together, the data suggest that this integrated droplet-based microfluidic platform provides an important tool for dynamic real time analysis of synaptic communications and downstream effector functions of immune cells.

Figure 10A:
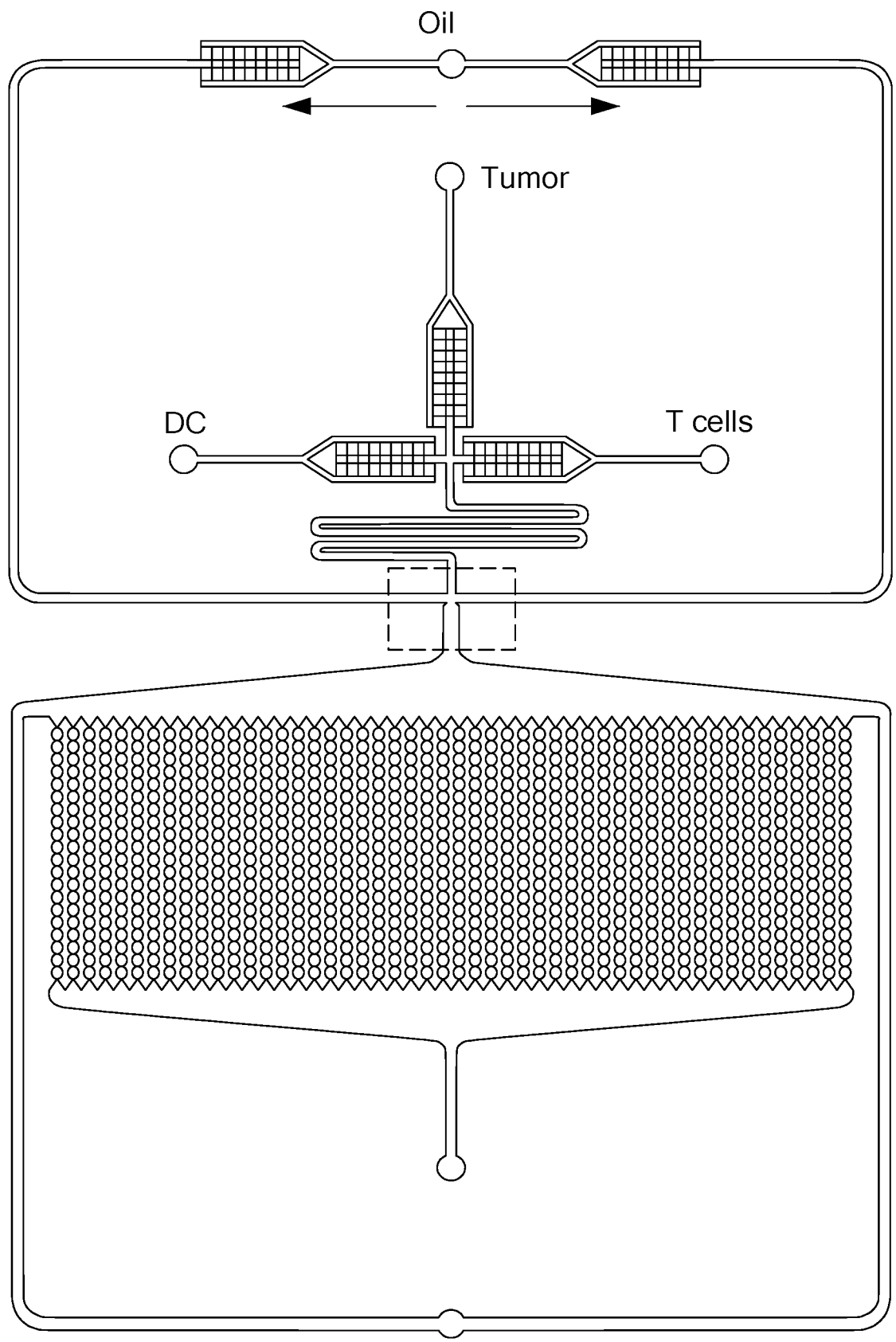

The microfluidic device was similar to that described above. The droplet generation junction was followed by a large docking array consisting of 1000 trapping sites where the droplets were stably arrested. Consistent droplet sizes of ~100 μm diameter (i.e., 520 pL volume) were obtained by optimization of the flow rates of the two phases (FIG. 10C). The cell encapsulated droplets were maintained for up to 48 hours in a $CO_2$-rich and humidified atmosphere, and minimal droplet shrinkage was observed. By coordinating individual inlet flow rates and optimizing initial cell density, large numbers of droplets were routinely obtained with co-encapsulation of all three types of individual cells (FIG. 10D).

Several types of cell co-encapsulation were performed using this approach: T-DC interaction, TDC-cancer cell interaction and NK-cancer cell interaction. unstimulated T cells derived from the non-adherent fraction of peripheral blood mononuclear cells, and mature DCs generated from adherent mononuclear cells cultured with cytokines were added through separate inlets to ensure that cell pairing and subsequent activation occurred only in the droplets. Likewise, NK cells and cancer cells (RPMI-8226 cells, a multiple myeloma line) were co-encapsulated in droplets by flowing through separate fluid inlets, thus allowing the investigators to monitor the early signaling events and synapse formation in this platform. For these studies with two cell types, the third inlet was used to perfuse media only. Since droplets provide a culture platform highly compatible with non-adherent cells, it was possible to observe a number of morphological features of the encapsulated cells, including secretory vesicle formation (FIG. 10E), dendrite extension by DCs (FIG. 10F), and membrane blebbing prior to cell death (FIG. 10G). The results showed both continuous and intermittent interactions between cell pairs, leading to quantitative analysis of dynamic parameters corresponding to these interactions (FIG. 11). In addition, all cellular secretions remained undiluted within the droplets, leading to noncontact-mediated activation of co-encapsulated cells while minimizing stimulation of neighboring cells.

Figure 11A:
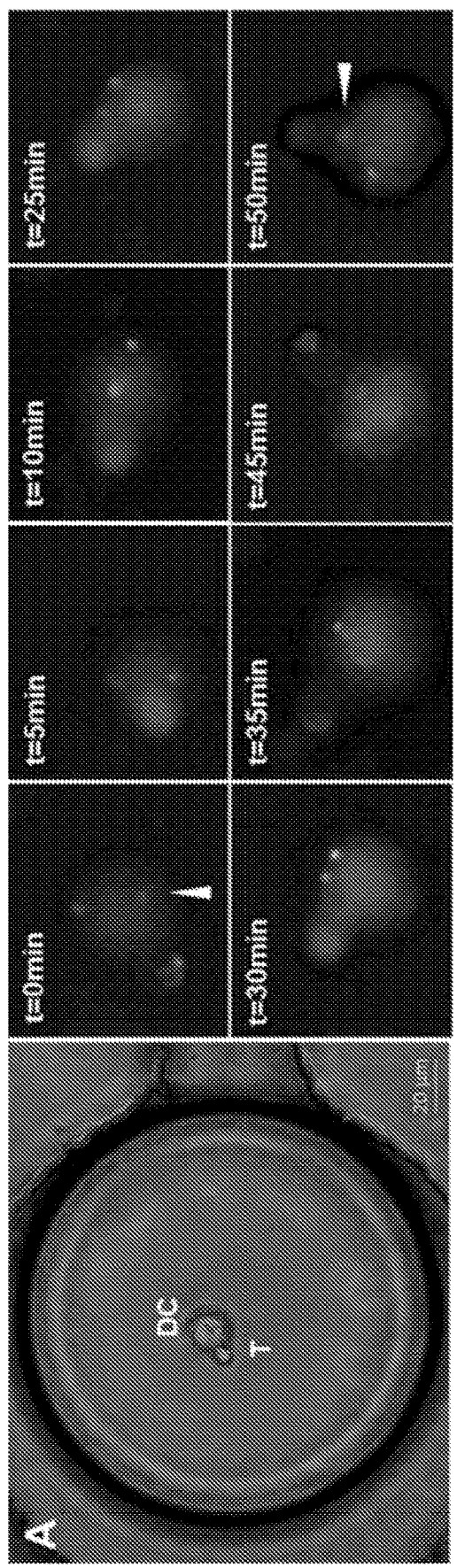
FIGS. 11A-11D show dynamic monitoring of interactions between activated DCs and T cells in microfluidic droplets.
Figure 11B:
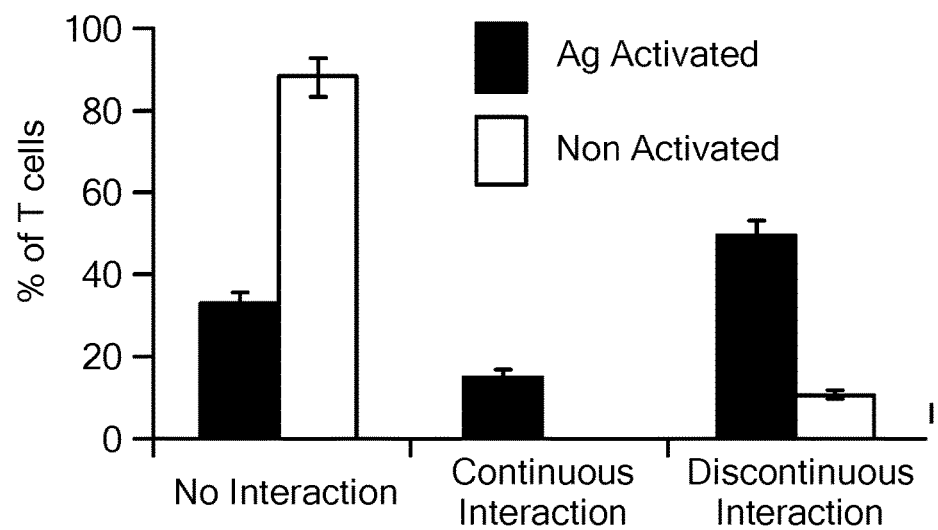
Figure 11C:
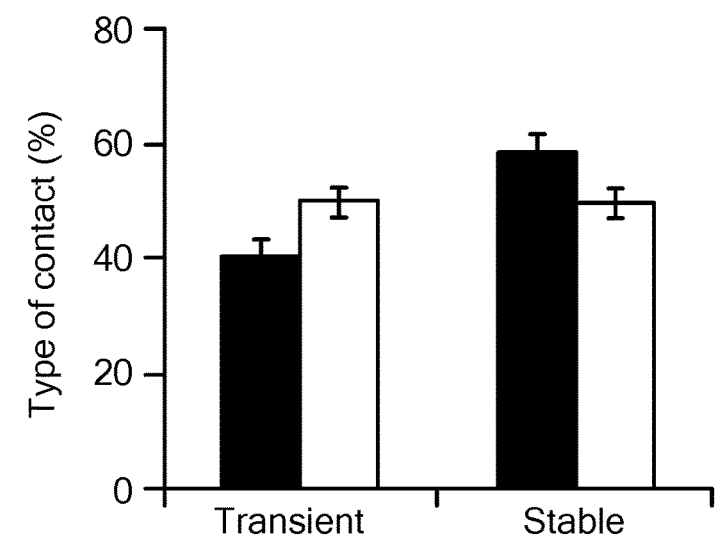
Figure 11D:
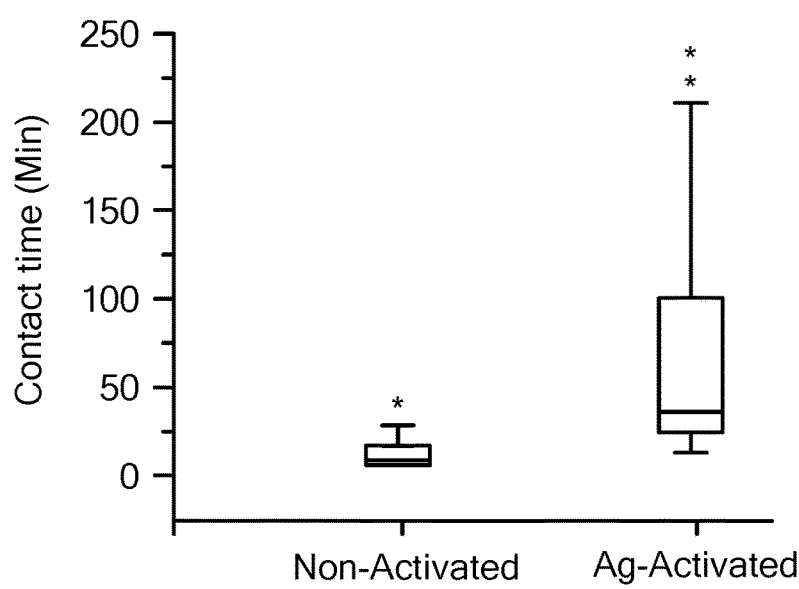

Mature DCs that had not specifically been loaded with Ag demonstrated relatively low interaction with non-stimulated T cells. Among the DC-T cell pairs co-encapsulated, 11% cells showed short periods of interaction while most did not interact at all (FIG. 11B). The duration of these interactions were either less than 10 minutes (50%), or 10-20 minutes (33%) (FIG. 11D). No interaction lasted longer than 35 minutes.

Next the dynamic interactions of chemokine-treated (CCL21), Ag-loaded DCs and naïve T cells was investigated at single cell resolution. DCs were exposed to FITC-conjugated OVA (323-329) peptides overnight, followed by treatment with CCL21 before co-encapsulation in droplets with naïve T cells (FIG. 11A). The presence of lymphoid chemokines such as CCR7 ligands CCL19 and CCL21 in the lymph node is known to regulate immune cell migration, maturation and effector functions. A marked increase in the extent of DC-T cell interaction was observed upon activation compared to control conditions (FIG. 11B). The dynamic single cell analysis also revealed strong heterogeneity in cellular interactions with respect to DC-T cell conjugate formation. While 34% of the T cells monitored showed no interaction with DCs, 16% remained conjugated throughout the duration of the experiment (5 hours). The conjugated cells showed lateral movement, in that the respective positions of the T cells on the surface of the DCs changed with time (FIG. 11A, right panel). The OVA-FITC peptide was observed expressed on the DC surface. Initially the T cell and the DC formed a synapse away from the site bearing the OVA-FITC peptide, but the contact site altered over time and eventually settled at the site of the Ag at 50 minutes. This motility of T cells was observed in almost all T-DC conjugates; however, the time required to reach the Ag-bearing site varied widely between cells.

A large proportion of the T cells observed (50%) interacted discontinuously and asynchronously with the co-encapsulated DCs, forming short term contacts and disassociating repeatedly (FIG. 11B). Here, transient interaction was defined by <10 minutes of cell complex retention. Longer interactions were considered stable. As indicated in FIG. 11C, 58% of the T cells undergoing discontinuous interaction depicted periods of stable contacts. While the duration of the contacts varied from cell to cell, the majority of the contacts lasted ≤40 minutes (FIG. 11D).

In addition to DCs activated with non-clinical triggering signals, the efficacy of DCs expressing tumor antigen in priming of T cell effector responses against a MM cell line was investigated in microdroplets. Dendritic cell (DC)-based vaccines are being pursued as therapeutic agents in an effort to induce clinically meaningful anti-tumor immunity. Hybridomas generated by fusion of patient-derived myeloma cells and autologous DCs present a broad array of tumor associated antigens in the context of DC mediated co-stimulation. In a clinical trial of patients undergoing autologous transplantation, vaccination with DC/MM fusions post-transplant resulted in the dramatic expansion of myeloma specific T cells and the conversion of partial to complete response in a subset of patients. In this study, DC vaccine cells activated with tumor lysate were utilized, together with DC/MM fusion cells. DCs matured by exposure to RPMI-8226 cell lysates were co-encapsulated with unprimed T cells and RPMI-8226 cells in droplets (FIG. 12A-12C). All three cells were initially separated and freely motile, as illustrated schematically in FIG. 12A and demonstrated in droplets in FIGS. 12B and 12C. Sequential interaction of the cell types occurred in the droplets, with DCs interacting with T cells first (FIGS. 12A-C(b)), followed by T-cancer cell interaction (FIGS. 12A-C(c)), thereby recapitulating the succession of events observed physiologically. Three distinct time phases were observed in the droplets. Firstly, the DCs loaded with tumor antigens demonstrated transient physical contact with T cells in the order of ≤10-20 minutes. Then the DC and T cell separated and a variable period of segregation was observed where all three cell types remained unattached. In the third phase, T cells formed conjugates with the RPMI-8226 cell for a period of ~20-30 minutes, which ended with cancer cell death (FIGS. 12A-C(e), (f)). These interactions took place over a total time period of 2 hours, although the duration of DC-T interaction and T-cancer interaction was heterogeneous between droplets. Furthermore, cancer cell death occurred in two ways, either in conjugation with the T cell or following separation of the cancer-T cell complex. Cancer cell death was most commonly observed by cell blebbing and membrane rupture, as well as uptake of ethidium homodimer (FIGS. 12A-C(f)). These results demonstrate that presentation of whole tumor derived antigen as lysate or DC/tumor hybridoma results in the productive interaction between DC and T cells resulting in T cell activation. While T cell activation appeared to be dependent on the presence of antigen, killing in this model was directed against allogeneic myeloma cell lines.

Example 5: Measurement of T Cell Activation by Dendritic Cells

The inventors tested whether the microfluidic droplet platform was suitable for monitoring calcium signaling in T cells following interaction with DCs. DCs were stimulated with 100 μg/mL ovalbumin (OVA (323-329)) peptide conjugated with FITC (Anaspec, Fremont, Calif.). The overall peptide sequence was FITC-LC-IS QAV HAA HAE INE AGR-OH. The DCs were treated overnight so as to promote antigen presentation on Major Histocompatibility Complex II (MHC-II). The DCs were washed twice to remove the suspended OVA-FITC in solution prior to encapsulation within droplets. The stimulated dendritic cells and T cells pre-loaded with the calcium indicator Fluo-4 were introduced from different inlets. Monitoring of cell-cell contact and intracellular calcium signaling began immediately after droplet generation and stable docking in the trapping array.

In the lymph node, DCs are known to scan T cell populations in an attempt to locate T cells of appropriate antigenic specificity. DCs form both transient and stable contact with T cells during antigen presentation, promoting T cell maturation, signaling and proliferation. Immune synapse formation between DCs and antigen presenting cells (APC) has been replicated in vitro; however, given that T cells are non-adherent, it is difficult to follow dynamic cell interaction of the same cell pair over prolonged periods without constraining cell motility through adhesion proteins or antibodies. Microfluidic droplets can circumvent this problem by co-encapsulating DCs and T cells within nanoliter volumes, thereby reducing cellular diffusion times while permitting directed and random motility, cell conjugation and dissociation as well as the possibility of repeated interaction between each cell pair.

Figure 13A:
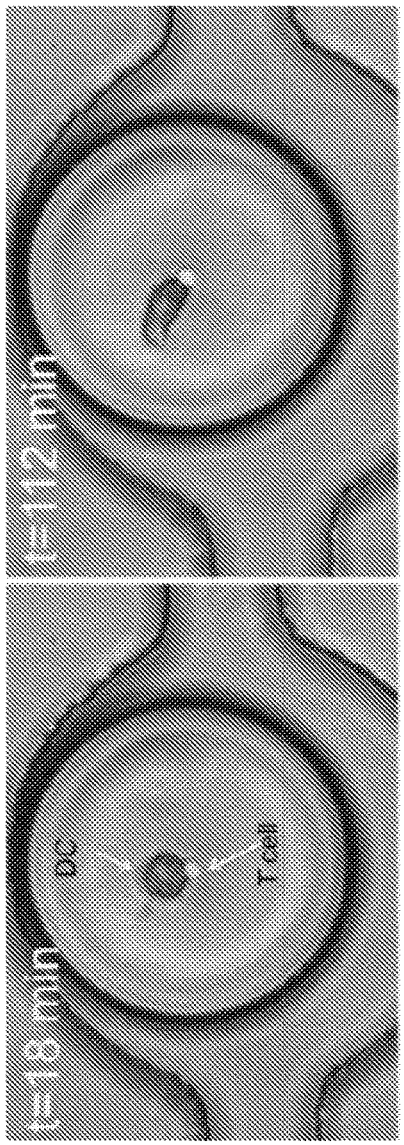
FIGS. 13A-13D show DC-T cell interaction and dynamic calcium signaling in droplets.
Figure 13B:
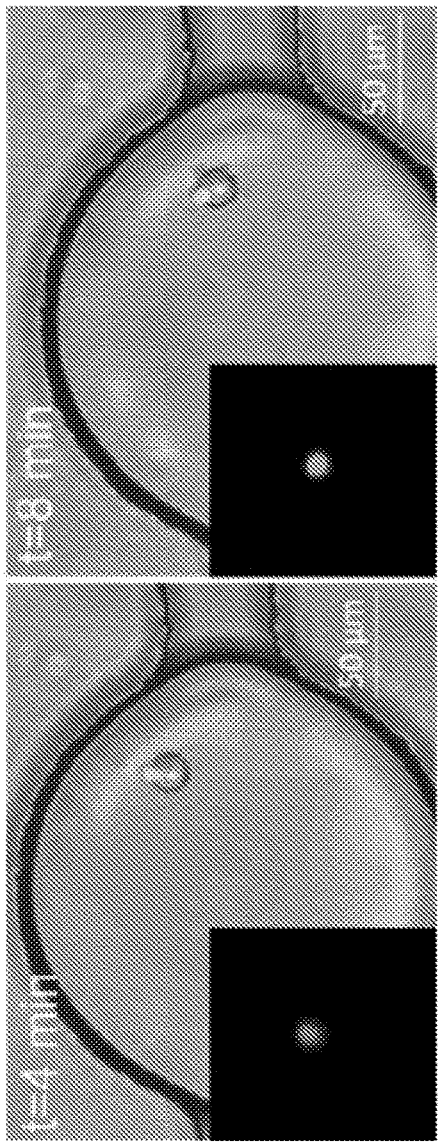
Figure 13C:
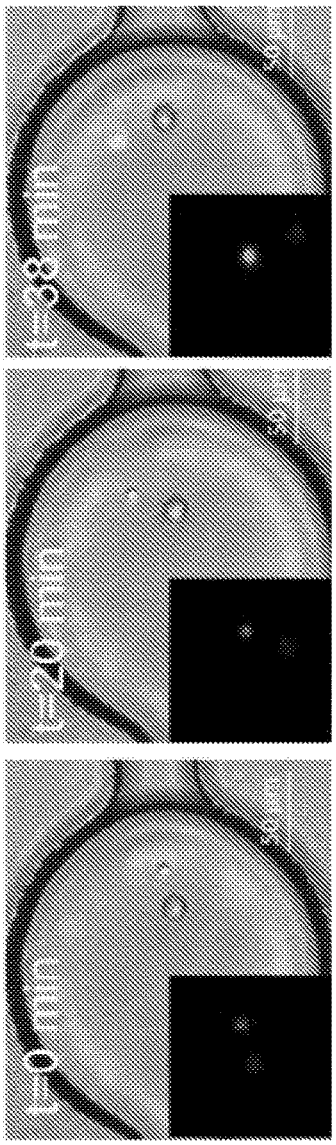

DCs were stimulated with FITC-conjugated ovalbumin (referred to as OVA-DC) peptide, a commonly used antigen that is ingested by DCs and presented to naïve T cells in a major histocompatibility complex II-bound manner. Co-encapsulation of DCs with T cells in the microfluidic droplet array resulted in long-lasting (≥90 minutes) as well as transient interaction of the two cell types (FIG. 13A). Within droplets, DCs depicted remarkable morphological changes and frequently extended dendrites, implying that DCs were able to function adequately in this microenvironment. An increase in cytosolic calcium transients was observed in the T cell following interaction of the two types of cell (FIG. 13B). This increase was extremely rapid and diminished over time even when the DC-T conjugate persisted, suggesting the end of early activation phase following initial contact (FIG. 13D(a)). Of note, the trends of the transient calcium increase in the T cells stimulated by OVA-DC were remarkably different compared to that observed in ionomycin-stimulated T cells. Here fluorescence intensity was observed to increase in narrow peaks, suggesting calcium spikes rather than broad fluctuations or consistent increase/decrease.

Figure 13D:
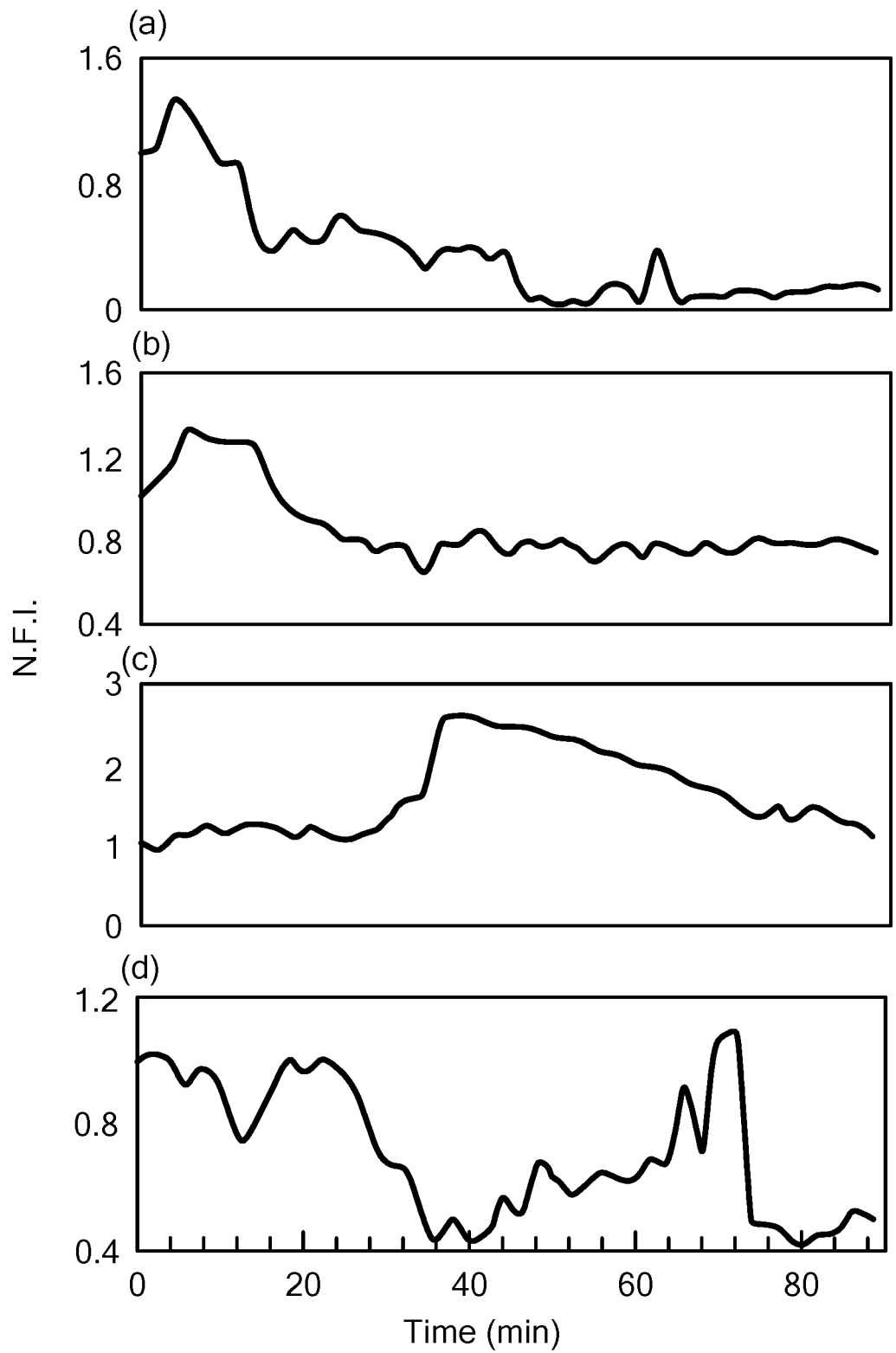

Interestingly, T cells showed a non-contact mediated increase in calcium signaling (FIG. 13D(cd)). This was observed at later time points compared to the OVA-DC-contact mediated increase in calcium levels, starting after approximately 30 minutes post-encapsulation. The duration and peak of the increased calcium levels differed from cell to cell. The mature DCs and T cells were sequestered in minute volumes in the droplets, which serve as nanoliter bioreactors and prevents dilution of cell-secreted products. It is feasible that the DCs activated T cells despite the lack of the contact via paracrine signaling.

Example 6: IgE-Dependent Manifestations of Allergy in Immune Cells

Figure 14:
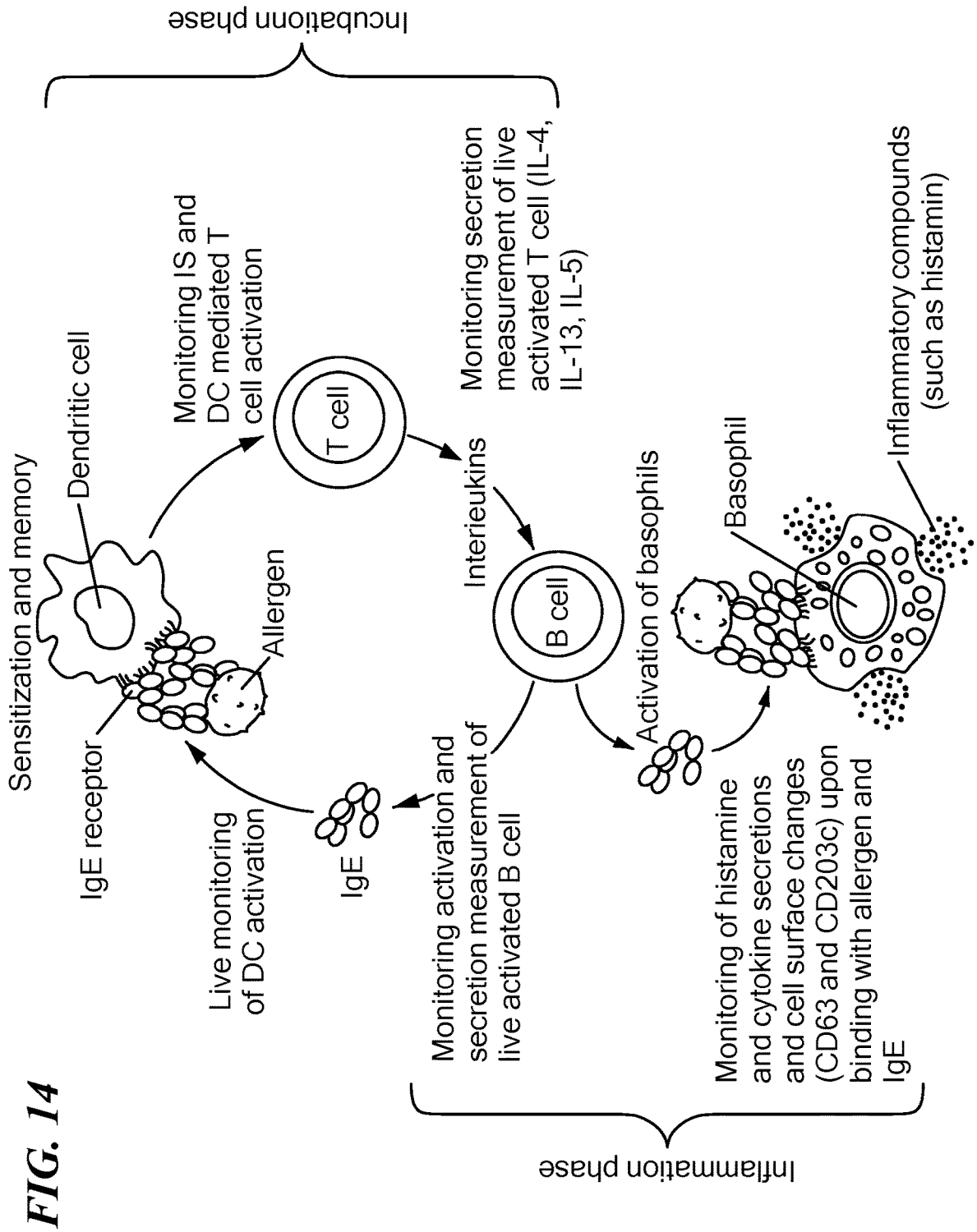
FIG. 14 is a schematic illustration of IgE-dependent cellular responses to allergy.

Immediate hypersensitivity (allergy) to foods is dependent upon allergen-specific IgE with exceptions for less common forms of food allergy such as eosinophilic esophagitis and other gastrointestinal conditions. Immune responses that regulate the allergen-specific IgE, IgG, and IgA repertoire—all of which likely contribute to clinical heterogeneity—depend upon cell-cell interactions such as those between dendritic cells and CD4 T cell subsets (see FIG. 14). In addition, IL-4, IL-5, and IL-13, produced by allergen-specific CD4 Th2 cells, play a major role in driving Th2 differentiation and induces IgE production by allergen-specific B cells (FIG. 14). Therefore, characterization of differences in DC responses and DC-T cell interactions between human food-allergic and non-allergic subjects is necessary to gain a better insight into the role of DCs in sensitization and tolerance to food allergens.

Basophils express the high affinity receptor for IgE (FceRI) and represent a significant population of antigen-specific cells in IgE-sensitized individuals that are capable of releasing histamine, leukotrienes, cytokines and other mediators. As such, basophils are both relevant tiomarkers' of IgE-mediated hypersensitivity and potential targets of immunomodulatory interventions. In fact, assays of IgE-dependent cellular responses, such as the basophil activation test (BAT), have already been shown to be more informative than assays simply detecting the presence of IgE but because they are less feasible, they have been less studied and not broadly pursued for clinical application. Furthermore distinct phenotypes of basophils with potential relation to clinical allergy and therapeutic potential of targeting basophils in preventing or alleviating the development and progression of allergic inflammation have been proposed. Thus it is important to study the effects of immunotherapy on basophil to better understand mechanisms of immunotherapy and evaluate basophil suppression as a biomarker for immunotherapy.

The use of the microfluidic devices and microdroplet-based encapsulation of the present invention is used to encapsulate and analyze individually specific functional phenotypes of cells relevant to allergy, such as food allergy. In addition, to cell surface studies, this approach is used to collect data on secreted molecules of single live cells or during DC-T synapse formation utilizing microsphere based fluorescence assays which are co-encapsulated in the microfluidic reaction droplets along with interrogated cells. Secreted molecules from single cells compartmentalized in the nanoliter droplet bioreactors quickly reach detectable concentrations because of the small droplet volume which allows rapid detection of live cellular secretion. Thus live cell secretion and surface monitoring are obtained simultaneously in a distinct microenvironment between two interacting cells, which previously was possible using complicated and multi-step in vitro and in vivo live-cell microscopy, together with immunological studies of the outcome secretion of cellular interactions. In addition, a fluorescence activated droplet sorting (FADS) system is used to collect subpopulations of immune cells having selected phenotypes.

Figure 15:
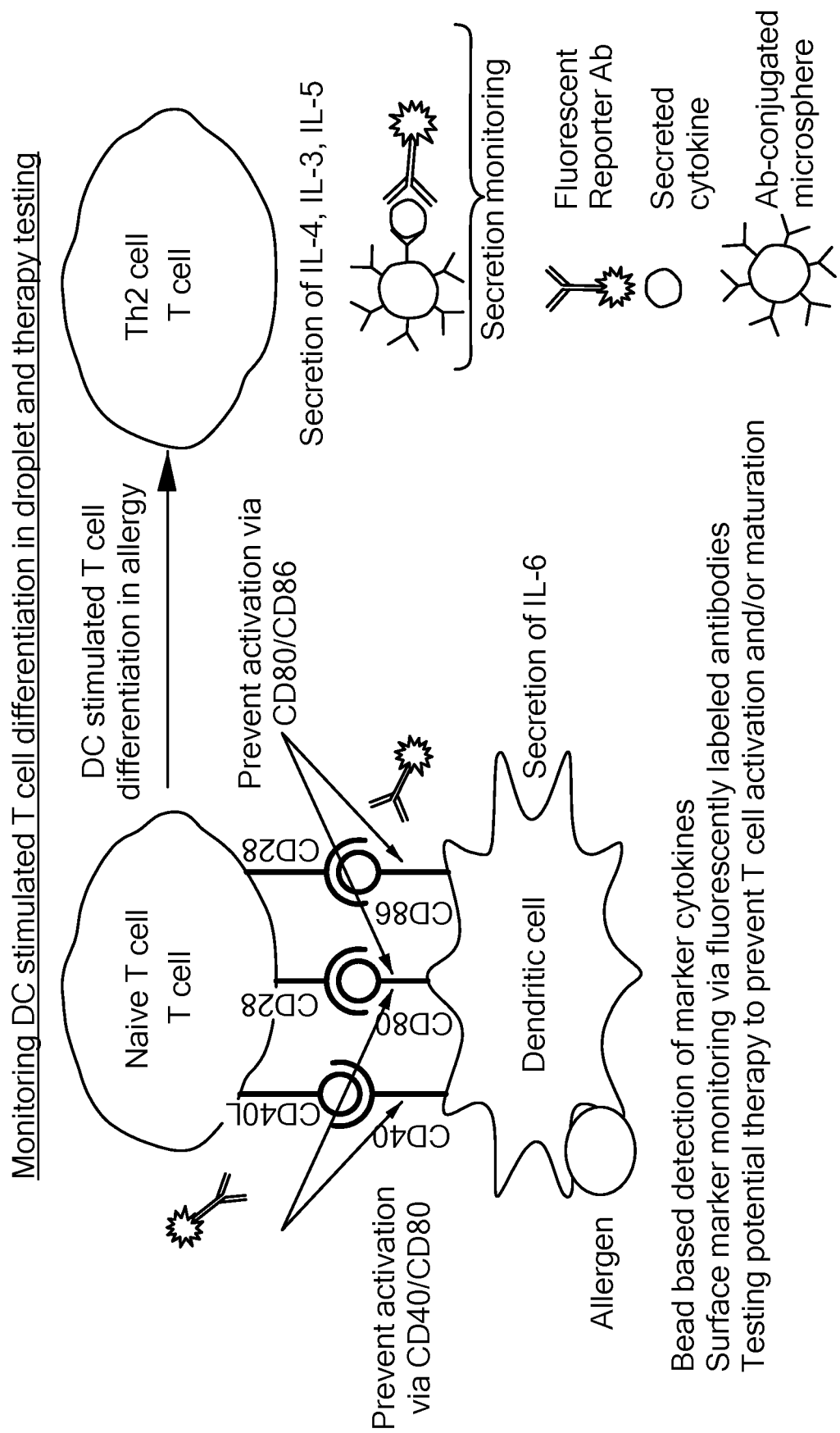
FIG. 15 is a schematic illustration of an allergen-driven, dendritic cell mediated maturation process of a T cell to a Th2 cell. The figure shows several receptors and secretion monitoring targets that can be used to follow the process.

The expression of CD86 can be followed in co-encapsulated T cells and DC, as a reflection of the co-stimulatory signals necessary for T cell activation (see FIG. 15). The interaction between CD40 on DC and its T cell ligand (CD40L) also can be followed to establish efficient activation of Th2 cell phenotype in droplets during immunological synapse formation. The co-encapsulation of T cell and DC in micro-reaction droplets is accompanied by bioassay reagents including fluorescently labeled anti-CD86 antibodies Cyanine 5(Cy5 red) and anti-CD40L antibodies Fluorescein isothiocyanate (FITC green). The maturation phenotype of the DC also can be followed by measuring IL-6, a cytokine that plays an important role in lymphocyte activation, as well as IL-4, IL-13, and IL-5 cytokines, secreted by Th2 cells (FIG. 15). For these cytokine secretion measurements during DC-T cell interactions, the cells are co-encapsulated along with fluorescently labeled detection antibodies (anti-IL-6 FITC, anti-IL-4 Cy3, anti-IL-5 Cy5, anti-IL-15 APC antibodies) and four microsphere sensors—SPHERO™ Avidin Coated Particles (0.9 µm) conjugated with 40 µg biotinylated IL-6, IL-4, IL-13, and IL-5 antibodies (FIG. 15).

Three assays that have been applied recently to food allergens are based on IgE-dependent basophil activation: the histamine release test, the CD63-based basophil-test, and the CD203c-activation assay. The co-encapsulation chip technology can be used for co-encapsulation of previously IgE sensitized basophils with crude peanut extract, in micro-reaction droplets along with bioassay reagents which are fluorescently labeled detection anti-CD63 antibodies (Cy5), anti-CD203c antibodies (FITC), as well as anti-histamine antibodies Cy3 (see FIG. 16A). The increase in CD63 and CD203c markers in response to an allergen as an increase in fluorescence over time also can be studied. In addition, allergen-induced (IgE-mediated) histamine release can be measured in a dose-dependent microdroplet reaction. Specific phenotypes of basophils could be obtained off chip using FADS technology.

Figure 16B:
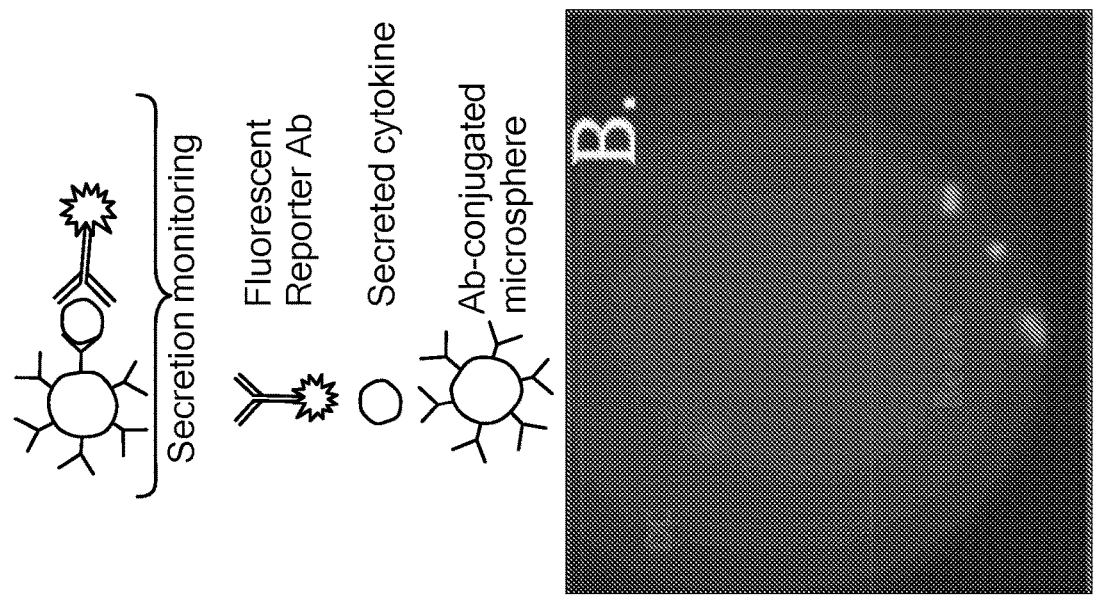
FIG. 16B shows lipopolysaccharide induced IL-6 secretion from single dendritic cells.
Figure 16A:
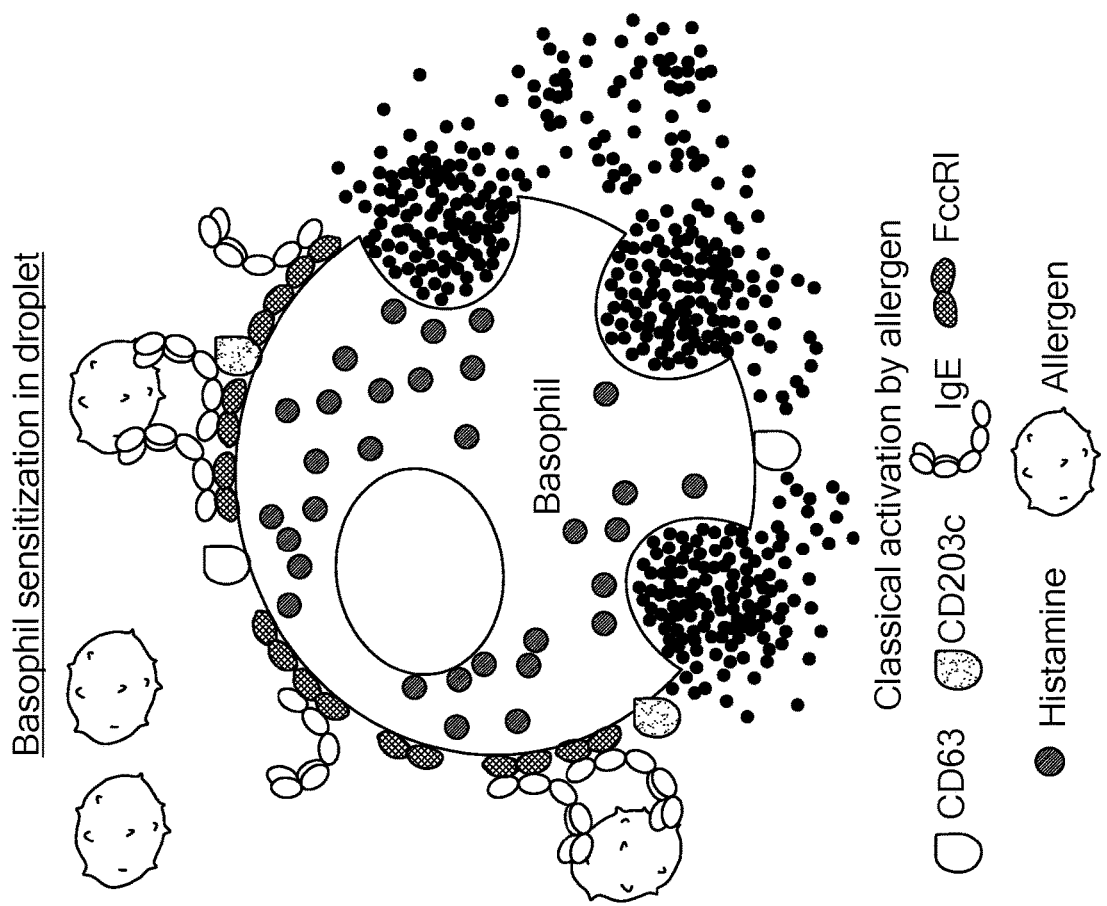
FIG. 16A is a schematic illustration of IgE-dependent basophil activation process carried out in a microdroplet.

The activation and monitoring of live single cells for secretion and cell surface markers have been measured simultaneously. In particular, droplet based technology can be applied to simultaneously stimulate mouse DC maturation with an immunological adjuvant, lipopolysaccharide (LPS), and to monitor two phenotypic markers of DCs. The maturation phenotype of the live DC was followed by measuring CD86 expression and IL-6 secretion. DC were co-encapsulated with LPS and bioassay reagents (microsphere sensors and antibodies). This method made it possible to distinguish the responses of individual cells to LPS stimulation in the confined volume of droplets. In addition to CD86, LPS induced IL-6 secretion could be monitored from the same encapsulated single DCs (FIG. 16B). The signal was detected in droplets after 10 min in the array. Droplets with LPS stimulation contained IL-6 levels that were significantly higher than droplets with no LPS, which showed negligible IL-6 levels.

REFERENCES

1. Hooton T M: Fluoroquinolones and resistance in the treatment of uncomplicated urinary tract infection. International journal of antimicrobial agents 2003, 22 Suppl 2:65-72.
2. Gupta K, Hooton T M, Naber K G, Wullt B, Colgan R, Miller L G, Moran G J, Nicolle L E, Raz R, Schaeffer A J, Soper D E: International clinical practice guidelines for the treatment of acute uncomplicated cystitis and pyelonephritis in women: A 2010 update by the Infectious Diseases Society of America and the European Society for Microbiology and Infectious Diseases. Clin Infect Dis 2011, 52(5):e103-120.
3. Barber A E, Norton J P, Spivak A M, Mulvey M A: Urinary tract infections: current and emerging management strategies. Clinical infectious diseases: an official publication of the Infectious Diseases Society of America 2013, 57(5):719-724. PMCID: 3739462
4. Nordmann P, Cuzon G, Naas T: The real threat of *Klebsiella pneumoniae* carbapenemase-producing bacteria. Lancet Infect Dis 2009, 9(4):228-236.
5. Kumarasamy K K, Toleman M A, Walsh T R, Bagaria J, Butt F, Balakrishnan R, Chaudhary U, Doumith M, Giske C G, Irfan S, Krishnan P, Kumar A V, Maharjan S, Mushtaq S, Noorie T, Paterson D L, Pearson A, Perry C, Pike R, Rao B, Ray U, Sarma J B, Sharma M, Sheridan E, Thirunarayan M A, Turton J, Upadhyay S, Warner M, Welfare W, Livermore D M, Woodford N: Emergence of a new antibiotic resistance mechanism in India, Pakistan, and the UK: a molecular, biological, and epidemiological study. Lancet Infect Dis 2010, 10(9):597-602. PMCID: 2933358
6. Detection of Enterobacteriaceae isolates carrying metallo-beta-lactamase—United States, 2010. MMWR Morb Mortal Wkly Rep 2010, 59(24):750.
7. Dortet L, Poirel L, Nordmann P: Worldwide Dissemination of the NDM-Type Carbapenemases in Gram-Negative Bacteria. Biomed Res Int 2014, 2014:249856. PMCID: 3984790
8. Spellberg B, Guidos R, Gilbert D, Bradley J, Boucher H W, Scheld W M, Bartlett J G, Edwards J, Jr.: The epidemic of antibiotic-resistant infections: a call to action for the medical community from the Infectious Diseases Society of America. Clinical infectious diseases: an official publication of the Infectious Diseases Society of America 2008, 46(2):155-164.

9. Won S Y, Munoz-Price L S, Lolans K, Hota B, Weinstein R A, Hayden M K: Emergence and rapid regional spread of *Klebsiella pneumoniae* carbapenemase-producing Enterobacteriaceae. Clinical infectious diseases: an official publication of the Infectious Diseases Society of America 2011, 53(6):532-540.
10. van Duin D, Perez F, Rudin S D, Cober E, Hanrahan J, Ziegler J, Webber R, Fox J, Mason P, Richter S S, Cline M, Hall G S, Kaye K S, Jacobs M R, Kalayjian R C, Salata R A, Segre J A, Conlan S, Evans S, Fowler V G, Jr., Bonomo R A: Surveillance of Carbapenem-Resistant *Klebsiella pneumoniae*: Tracking Molecular Epidemiology and Outcomes through a Regional Network. Antimicrobial agents and chemotherapy 2014.
11. Hirsch E B, Tam V H: Detection and treatment options for *Klebsiella pneumoniae* carbapenemases (KPCs): an emerging cause of multidrug-resistant infection. J Antimicrob Chemother 2010, 65(6):1119-1125.
12. Munson E L, Diekema D J, Beekmann S E, Chapin K C, Doern G V: Detection and treatment of bloodstream infection: laboratory reporting and antimicrobial management. Journal of clinical microbiology 2003, 41(1):495-497. PMCID: 149611
13. Clark A E, Kaleta E J, Arora A, Wolk D M: Matrix-assisted laser desorption ionization-time of flight mass spectrometry: a fundamental shift in the routine practice of clinical microbiology. Clin Microbiol Rev 2013, 26(3): 547-603. PMCID: 3719498
14. Tam V H, Hirsch E B, Lasco T M, Gentry L O, Palmer H R: Correlation of hospital carbapenem consumption and resistance trends in selected gram-negative bacteria. Ann Pharmacother 2012, 46(7-8):1120-1122.
15. Aitken S L, Beyda N D, Shah D N, Palmer H R, Lasco T M, Koo H, Garey K W: Clinical practice patterns in hospitalized patients at risk for invasive candidiasis: role of antifungal stewardship programs in an era of rapid diagnostics. The Annals of pharmacotherapy 2014, 48(6): 683-690.
16. van Belkum A, Durand G, Peyret M, Chatellier S, Zambardi G, Schrenzel J, Shortridge D, Engelhardt A, Dunne W M, Jr.: Rapid clinical bacteriology and its future impact. Ann Lab Med 2013, 33(1):14-27. PMCID: 3535192
17. Tan K E, Ellis B C, Lee R, Stamper P D, Zhang S X, Carroll K C: Prospective evaluation of a matrix-assisted laser desorption ionization-time of flight mass spectrometry system in a hospital clinical microbiology laboratory for identification of bacteria and yeasts: a bench-by-bench study for assessing the impact on time to identification and cost-effectiveness. Journal of clinical microbiology 2012, 50(10):3301-3308. PMCID: 3457442
18. Coombs G W, Morgan J P, Tan H L, Pearson J C, Robinson J O: Evaluation of the BD GeneOhm MRSA ACP Assay and the Cepheid GeneXpert MRSA Assay to detect genetically diverse CA-MRSA. Pathology 2013, 45(7):713-715.
19. Tenover F C, Canton R, Kop J, Chan R, Ryan J, Weir F, Ruiz-Garbajosa P, LaBombardi V, Persing D H: Detection of colonization by carbapenemase-producing Gram-negative Bacilli in patients by use of the Xpert MDRO assay. Journal of clinical microbiology 2013, 51(11):3780-3787. PMCID: 3889767
20. Park K S, Kim J Y, Lee J W, Hwang Y Y, Jeon K, Koh W J, Ki C S, Lee N Y: Comparison of the Xpert MTB/RIF and Cobas TaqMan MTB assays for detection of *Mycobacterium tuberculosis* in respiratory specimens. Journal of clinical microbiology 2013, 51(10):3225-3227. PMCID: 3811628
21. Baron E J, Tenover F C: Methicillin-resistant *Staphylococcus aureus* diagnostics: state of the art. Expert Opin Med Diagn 2012, 6(6):585-592.
22. Baker I, Leeming J P, Reynolds R, Ibrahim I, Darley E: Clinical relevance of a positive molecular test in the diagnosis of *Clostridium difficile* infection. The Journal of hospital infection 2013, 84(4):311-315.
23. D'Andrea M M, Venturelli C, Giani T, Arena F, Conte V, Bresciani P, Rumpianesi F, Pantosti A, Narni F, Rossolini G M: Persistent carriage and infection by multidrug-resistant *Escherichia coli* ST405 producing NDM-1 carbapenemase: report on the first Italian cases. Journal of clinical microbiology 2011, 49(7):2755-2758. PMCID: 3147842
24. Hannan T J, Totsika M, Mansfield K J, Moore K H, Schembri M A, Hultgren S J: Host-pathogen checkpoints and population bottlenecks in persistent and intracellular uropathogenic *Escherichia coli* bladder infection. FEMS Microbiol Rev 2012, 36(3):616-648. PMCID: 3675774
25. Otto G, Braconier J, Andreasson A, Svanborg C: Interleukin-6 and disease severity in patients with bacteremic and nonbacteremic febrile urinary tract infection. The Journal of infectious diseases 1999, 179(1):172-179.
26. Olszyna D P, Prins J M, Dekkers P E, De Jonge E, Speelman P, Van Deventer S J, Van Der Poll T: Sequential measurements of chemokines in urosepsis and experimental endotoxemia. J Clin Immunol 1999, 19(6):399-405.
27. Hedges S, Stenqvist K, Lidin-Janson G, Martinell J, Sandberg T, Svanborg C: Comparison of urine and serum concentrations of interleukin-6 in women with acute pyelonephritis or asymptomatic bacteriuria. The Journal of infectious diseases 1992, 166(3):653-656.
28. Ciszek M, Paczek L, Bartlomiejczyk I, Mucha K: Urine cytokines profile in renal transplant patients with asymptomatic bacteriuria. Transplantation 2006, 81(12):1653-1657.
29. Fischer K, Hamza A, Eismann R, Amoury M, Heynemann H, Fornara P: Differential diagnostic use of interleukin patterns in patients being monitored after transplantation. Clin Chim Acta 2001, 310(1):71-80.
30. Hedges S, Svanborg C: The mucosal cytokine response to urinary tract infections. International journal of antimicrobial agents 1994, 4(2):89-93.
31. Samuelsson P, Hang L, Wullt B, Irjala H, Svanborg C: Toll-like receptor 4 expression and cytokine responses in the human urinary tract mucosa. Infect Immun 2004, 72(6):3179-3186. PMCID: 415697
32. Godaly G, Ambite I, Svanborg C: Innate immunity and genetic determinants of urinary tract infection susceptibility. Current opinion in infectious diseases 2015, 28(1): 88-96. PMCID: 4286230
33. Rodriguez L M, Robles B, Marugan J M, Suarez A, Garcia Ruiz de Morales J M: Do serum C-reactive protein and interleukin-6 predict kidney scarring after urinary tract infection? Indian J Pediatr 2013, 80(12):1002-1006.
34. Renata Y, Jassar H, Katz R, Hochberg A, Nir R R, Klein-Kremer A: Urinary concentration of cytokines in children with acute pyelonephritis. Eur J Pediatr 2013, 172(6):769-774.
35. Jantausch B A, O'Donnell R, Wiedermann B L: Urinary interleukin-6 and interleukin-8 in children with urinary tract infection. Pediatr Nephrol 2000, 15(3-4):236-240.

36. Ko Y C, Mukaida N, Ishiyama S, Tokue A, Kawai T, Matsushima K, Kasahara T: Elevated interleukin-8 levels in the urine of patients with urinary tract infections. Infect Immun 1993, 61(4):1307-1314. PMCID: 281363
37. Rodhe N, Lofgren S, Strindhall J, Matussek A, Molstad S: Cytokines in urine in elderly subjects with acute cystitis and asymptomatic bacteriuria. Scand J Prim Health Care 2009, 27(2):74-79. PMCID: 3410465
38. Joensson H N, Samuels M L, Brouzes E R, Medkova M, Uhlen M, Link D R, Andersson-Svahn H: Detection and analysis of low-abundance cell-surface biomarkers using enzymatic amplification in microfluidic droplets. Angew Chem Int Ed Engl 2009, 48(14):2518-2521.
39. Song H, Chen D L, Ismagilov R F: Reactions in droplets in microfluidic channels. Angew Chem Int Ed Engl 2006, 45(44):7336-7356. PMCID: 1766322
40. Agresti J J, Antipov E, Abate A R, Ahn K, Rowat A C, Baret J C, Marquez M, Klibanov A M, Griffiths A D, Weitz D A: Ultrahigh-throughput screening in drop-based microfluidics for directed evolution. Proc Natl Acad Sci USA 2010, 107(9):4004-4009. PMCID: 2840095
41. Kiss M M, Ortoleva-Donnelly L, Beer N R, Warner J, Bailey C G, Colston B W, Rothberg J M, Link D R, Leamon J H: High-throughput quantitative polymerase chain reaction in picoliter droplets. Anal Chem 2008, 80(23):8975-8981. PMCID: 2771884
42. Koster S, Angile F E, Duan H, Agresti J J, Wintner A, Schmitz C, Rowat A C, Merten C A, Pisignano D, Griffiths A D, Weitz D A: Drop-based microfluidic devices for encapsulation of single cells. Lab Chip 2008, 8(7):1110-1115.
43. Brouzes E, Medkova M, Savenelli N, Marran D, Twardowski M, Hutchison J B, Rothberg J M, Link D R, Perrimon N, Samuels M L: Droplet microfluidic technology for single-cell high-throughput screening. Proc Natl Acad Sci USA 2009, 106(34):14195-14200. PMCID: 2732882
44. Mazutis L, Araghi A F, Miller O J, Baret J C, Frenz L, Janoshazi A, Taly V, Miller B J, Hutchison J B, Link D, Griffiths A D, Ryckelynck M: Droplet-based microfluidic systems for high-throughput single DNA molecule isothermal amplification and analysis. Anal Chem 2009, 81(12):4813-4821.
45. Shum H C, Kim J W, Weitz D A: Microfluidic fabrication of monodisperse biocompatible and biodegradable polymersomes with controlled permeability. J Am Chem Soc 2008, 130(29):9543-9549.
46. Golberg A, Linshiz G, Kravets I, Stawski N, Hillson N J, Yarmush M L, Marks R S, Konry T: Cloud-Enabled Microscopy and Droplet Microfluidic Platform for Specific Detection of *Escherichia coli* in Water. PLoS One 2014, 9(1):e86341. PMCID: 3903517. See also PCT/US2014/010412.
47. Konry T, Golberg A, Yarmush M: Live single cell functional phenotyping in droplet nanoliter reactors. Sci Rep 2013, 3:3179. PMCID: 3822379
48. Konry T, Lerner A, Yarmush M L, Smolina I: Target DNA detection and quantitation on a single cell with single base resolution. Technology 2013, 88(1).
49. Konry T, Bale S S, Bhushan A, Shen K, Seker E, Polyak B, Yarmush M: Particles and microfluidics merged: perspectives of highly sensitive diagnostic detection. Mikrochim Acta 2012, 176(3-4):251-269. PMCID: 4219152
50. Konry T, Walt D R: Intelligent medical diagnostics via molecular logic. J Am Chem Soc 2009, 131(37):13232-13233. PMCID: 2750850
51. Konry T, Hayman R B, Walt D R: Microsphere-based rolling circle amplification microarray for the detection of DNA and proteins in a single assay. Anal Chem 2009, 81(14):5777-5782. PMCID: 2730947
52. Konry T, Dominguez-Villar M, Baecher-Allan C, Hafler D A, Yarmush M L: Droplet-based microfluidic platforms for single T cell secretion analysis of IL-10 cytokine. Biosens Bioelectron 2011, 26(5):2707-2710. PMCID: 3141325
53. LaFratta C N, Walt D R: Very high density sensing arrays. Chem Rev 2008, 108(2):614-637.
54. Gorris H H, Blicharz T M, Walt D R: Optical-fiber bundles. Febs J 2007, 274(21):5462-5470.
55. Di Padova F E, Brade H, Barclay G R, Poxton I R, Liehl E, Schuetze E, Kocher H P, Ramsay G, Schreier M H, McClelland D B, et al.: A broadly cross-protective monoclonal antibody binding to *Escherichia coli* and *Salmonella* lipopolysaccharides. Infect Immun 1993, 61(9):3863-3872. PMCID: 281087
56. Kuhn H M, Meier-Dieter U, Mayer H: ECA, the enterobacterial common antigen. FEMS Microbiol Rev 1988, 4(3):195-222.
57. Brade L, Podschun R, Brade H: A monoclonal antibody with specificity for the genus *Klebsiella* binds to a common epitope located in the core region of *Klebsiella* lipopolysaccharide. J Endotoxin Res 2001, 7(2):119-124.
58. DiGiandomenico A, Warrener P, Hamilton M, Guillard S, Ravn P, Minter R, Camara M M, Venkatraman V, Macgill R S, Lin J, Wang Q, Keller A E, Bonnell J C, Tomich M, Jermutus L, McCarthy M P, Melnick D A, Suzich J A, Stover C K: Identification of broadly protective human antibodies to *Pseudomonas aeruginosa* exopolysaccharide Psi by phenotypic screening. J Exp Med 2012, 209(7):1273-1287. PMCID: 3405507
59. Juskowiak B: Nucleic acid-based fluorescent probes and their analytical potential. Anal Bioanal Chem 2011, 399(9):3157-3176. PMCID: 3044240
60. Frickmann H, Essig A, Hagen R M, Riecker M, Jerke K, Ellison D, Poppert S: Rapid identification of *Acinetobacter* spp. by fluorescence in situ hybridization (FISH) from colony and blood culture material. Eur J Microbiol Immunol (Bp) 2011, 1(4):289-296. PMCID: 3918131
61. Priya N G, Pandey N, Rajagopal R: LNA probes substantially improve the detection of bacterial endosymbionts in whole mount of insects by fluorescent in-situ hybridization. BMC Microbiol 2012, 12:81. PMCID: 3536699
62. Kubota K, Ohashi A, Imachi H, Harada H: Improved in situ hybridization efficiency with locked-nucleic-acid-incorporated DNA probes. Appl Environ Microbiol 2006, 72(8):5311-5317. PMCID: 1538721
63. Chiaraviglio L, Kirby J E: Evaluation of impermeant, DNA-binding dye fluorescence as a real-time readout of eukaryotic cell toxicity in a high throughput screening format. Assay Drug Dev Technol 2014, 12(4):219-228. PMCID: 4026211
64. Burnham C A, Frobel R A, Herrera M L, Wickes B L: Rapid ertapenem susceptibility testing and *Klebsiella pneumoniae* carbapenemase phenotype detection in *Klebsiella pneumoniae* isolates by use of automated microscopy of immobilized live bacterial cells. Journal of clinical microbiology 2014, 52(3):982-986. PMCID: 3957783
65. Albers A C, Fletcher R D: Accuracy of calibrated-loop transfer. Journal of clinical microbiology 1983, 18(1):40-42. PMCID: 270741
66. www.fda.gov/ohrms/dockets/98fr/000109gd.pdf 67. Wu H, Wheeler A, Zare R N (2004) Chemical cytometry on a picoliter-scale integrated microfluidic chip. Proc Natl Acad Sci USA 101(35):12809-13.
68. Taff B M, Voldman J (2005) A scalable addressable positive-dielectrophoretic cell-sorting array. Anal Chem 77(24):7976-83.
69. Jaeger M S, Uhlig K, Schnelle T, and Mueller T (2008) Contact-free single-cell cultivation by negative dielectrophoresis. J. Phys. D: Appl. Phys. 41, 175502.
70. Werner M, Palankar R, Arm L, Hovius R, Vogel H (2015) Microfluidic Single-Cell Analysis with Affinity Beads. Small doi: 10.1002/smll.201402650.
71. Rettig J R, Folch A (2005) Large-scale single-cell trapping and imaging using microwell arrays. Anal Chem 77(17):5628-34.
72. Han Q, Bagheri N, Bradshaw E M, Hafler D A, Lauffenburger D A, et al. (2012) Polyfunctional responses by human T cells result from sequential release of cytokines. Proc Natl Acad Sci USA. 109(5):1607-12.
73. Faley S, Seale K, Hughey J, Schaffer D K, VanCompernolle S, et al. (2008) Microfluidic platform for real-time signaling analysis of multiple single T cells in parallel. Lab Chip 8(10):1700-12.
74. Chung K, Rivet C A, Kemp M L, Lu H (2011) Imaging single-cell signaling dynamics with a deterministic high-density single-cell trap array. Anal Chem 83(18):7044-52.
75. Chung J, Kim Y J, Yoon E (2011) Highly-efficient single-cell capture in microfluidic array chips using differential hydrodynamic guiding structures. Appl Phys Lett 98(12):123701.
76. Jin D, Deng B, Li J X, Cai W, Tu L, et al. (2015) A microfluidic device enabling high-efficiency single cell trapping. Biomicrofluidics 9(1):014101.
77. Zhang K, Chou C K, Xia X, Hung M C, Qin L (2014) Block-Cell-Printing for live single-cell printing. Proc Natl Acad Sci USA 111(8):2948-53.
78. Di Carlo D, Wu L Y, Lee L P (2006) Dynamic single cell culture array. Lab Chip. 6(11):1445-9.
79. Kobel S, Valero A, Latt J, Renaud P, Lutolf M (2010) Optimization of microfluidic single cell trapping for long-term on-chip culture. Lab Chip 10(7):857-63
80. Skelley A M, Kirak O, Suh H, Jaenisch R, Voldman J (2009) Microfluidic control of cell pairing and fusion. Nat Methods 6(2):147-52.

As used herein, "consisting essentially of" allows the inclusion of materials or steps that do not materially affect the basic and novel characteristics of the claim. Any recitation herein of the term "comprising", particularly in a description of components of a composition or in a description of elements of a device, can be exchanged with "consisting essentially of" or "consisting of".

While the present invention has been described in conjunction with certain preferred embodiments, one of ordinary skill, after reading the foregoing specification, will be able to effect various changes, substitutions of equivalents, and other alterations to the compositions and methods set forth herein.

The invention claimed is:

1. A method of analyzing a cell phenotype, the method comprising the steps of:
   (a) providing a microfluidic device capable of forming aqueous microdroplets in oil, the device comprising a translucent microdroplet array chamber and a microdroplet merging junction having a geometry that combines microdroplets together, and providing an imaging microscope;
   (b) preparing a plurality of aqueous microdroplets in oil using the microfluidic device, each microdroplet comprising a sample containing or suspected of containing one or more cells and one or more reagents for analyzing a phenotype of said cells;
   (c) adding one or more additional reagents to said aqueous microdroplets by merging each of said aqueous microdroplets with a reagent microdroplet comprising one or more additional reagents using said microdroplet merging junction to form a plurality of merged aqueous microdroplets;
   (d) directing the plurality of merged aqueous microdroplets into the microdroplet array chamber;
   (e) obtaining an image of the microdroplet array chamber using the imaging microscope; and
   (f) measuring an optical signal from said reagent, whereby information regarding the phenotype of said cells is obtained.

2. The method of claim 1, wherein the phenotype is activation of an immune response, and the cells comprise T lymphocytes.

3. The method of claim 1, wherein aqueous microdroplets are sorted and routed to a selected fluidic pathway, chamber, or off device location, according to the optical signal detected in the aqueous microdroplets.

4. The method of claim 2, wherein the reagent microdroplets comprise antigen presenting cells.

5. The method of claim 2, wherein the reagent microdroplets comprise tumor cells.

6. The method of claim 5, wherein the T lymphocytes and tumor cells are from the same subject.

7. The method of claim 2, wherein the reagent microdroplets comprise one or more reagents for detecting T cell activation.

8. The method of claim 1, wherein the reagent microdroplets comprise one or more reagents for detecting living or dead cells.

* * * * *